(12) United States Patent
Siewerdsen et al.

(10) Patent No.: US 10,478,148 B2
(45) Date of Patent: Nov. 19, 2019

(54) SELF-CALIBRATING PROJECTION GEOMETRY FOR VOLUMETRIC IMAGE RECONSTRUCTION

(71) Applicant: THE JOHNS HOPKINS UNIVERSITY, Baltimore, MD (US)

(72) Inventors: Jeffrey H. Siewerdsen, Baltimore, MD (US); Yoshito Otake, Baltimore, MD (US); Joseph Webster Stayman, Baltimore, MD (US); Ali Uneri, Baltimore, MD (US); Adam S. Wang, Baltimore, MD (US); Sarah Ouadah, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 84 days.

(21) Appl. No.: 15/436,042

(22) Filed: Feb. 17, 2017

(65) Prior Publication Data
US 2017/0238897 A1 Aug. 24, 2017

Related U.S. Application Data

(60) Provisional application No. 62/297,255, filed on Feb. 19, 2016.

(51) Int. Cl.
| | | |
|---|---|---|
| *G06K 9/00* | (2006.01) | |
| *A61B 6/00* | (2006.01) | |
| *A61B 6/03* | (2006.01) | |
| *A61B 6/02* | (2006.01) | |

(52) U.S. Cl.
CPC .............. *A61B 6/584* (2013.01); *A61B 6/025* (2013.01); *A61B 6/032* (2013.01); *A61B 6/4085* (2013.01); *A61B 6/4441* (2013.01); *A61B 6/466* (2013.01); *A61B 6/501* (2013.01); *A61B 6/5205* (2013.01)

(58) Field of Classification Search
None
See application file for complete search history.

(56) References Cited

PUBLICATIONS

Li, et al., A cone beam SPECT reconstruction algorithm with a displaced center of rotation. Medical Physics 1994, 21, 145.
(Continued)

*Primary Examiner* — Atiba O Fitzpatrick
(74) *Attorney, Agent, or Firm* — Johns Hopkins Technology Ventures

(57) ABSTRACT

The present invention is directed to a method for enabling volumetric image reconstruction from unknown projection geometry of tomographic imaging systems, including CT, cone-beam CT (CBCT), and tomosynthesis systems. The invention enables image reconstruction in cases where it was not previously possible (e.g., custom-designed trajectories on robotic C-arms, or systems using uncalibrated geometries), and more broadly offers improved image quality (e.g., improved spatial resolution and reduced streak artifact) and robustness to patient motion (e.g., inherent compensation for rigid motion) in a manner that does not alter the patient setup or imaging workflow. The method provides a means for accurately estimating the complete geometric description of each projection acquired during a scan by simulating various poses of the x-ray source and detector to determine their unique, scan-specific positions relative to the patient, which is often unknown or inexactly known (e.g., a custom-designed trajectory, or scan-to-scan variability in source and detector position).

20 Claims, 18 Drawing Sheets

(56) References Cited

PUBLICATIONS

Jaffray, et al., Flat-panel cone-beam computed tomography for image-guided radiation therapy. International Journal of Radiation Oncology Biology Physics 2002, 53, 1337-1349.
Fahrig, et al., Three-dimensional computed tomographic reconstruction using a C-arm mounted XRII: Image-based correction of gantry motion nonidealities. Medical Physics 2000, 27, 30.
Jain, et al., C-arm calibration—is it really necessary? SPIE Medical Imaging 2007, 65092.
Dennerlein, et al., Geometric jitter compensation in cone-beam CT through registration of directly and indirectly Filtered projections. 2012 IEEE Nuclear Science Symposium and Medical Imaging Conference Record 2012, 2892-2895.
Stayman, et al., Task-based trajectories in iteratively reconstructed interventional cone-beam CT. The 12th International Meeting on Fully Three-Dimensional Image Reconstruction in Radiology and Nuclear Medicine 2013, 257-260.
Yu, et al., Data consistency based rigid motion artifact reduction in fan-beam CT. IEEE Transactions on Medical Imaging 2007, 26, 249-260.
Wang, et al., Soft-tissue imaging with C-arm cone-beam CT using statistical reconstruction. Physics in Medicine and Biology 2014, 59, 1005-1029.
Navab, et al., 3D reconstruction from projection matrices in a C-arm based 3D-angiography system. Medical Image Computing and Computer-Assisted Intervention 1998, 1496, 119-129.
Galigekere, et al., Cone-beam reprojection using projectionmatrices. IEEE Transactions on Medical Imaging 2003, 22, 1202-1214.
Strobel, et al., Improving 3D image quality of x-ray C-arm imaging systems by using properly designed pose determination systems for calibrating the projection geometry. SPIE Medical Imaging 2003, 943-954.
Daly, et al., Geometric calibration of a mobile C-arm for intraoperative cone-beam CT. Medical Physics 2008, 35, 2124.
Cho, et al., Accurate technique for complete geometric calibration of cone-beam computed tomography systems. Medical Physics 2005, 32, 968.
Yang, et al., A geometric calibration method for cone beam CT systems. Medical Physics 2006, 33, 1695.
Zhang, et al., Objective characterization of GE discovery CT750 HD scanner: gemstone spectral imaging mode. Medical Physics 2011, 38, 1178-1188.
Navab, et al., Dynamic geometrical calibration for 3D cerebral angiography. Proceedings of SPIE 1996, 2708, 361.
Tate, et al., Performance and Robustness of Automatic Fluoroscopic Image Calibration in a New Computer Assisted Surgery System. Medical Image Computing and Computer-Assisted Intervention 2001, 2208, 1130-1136.
Livyatan, et al., Robust Automatic C-Arm Calibration for Fluoroscopy-Based Navigation: A Practical Approach. Medical Image Computing and Computer-Assisted Intervention 2002, 2489, 60-68.
Smekal, et al., Geometric misalignment and calibration in cone-beam tomography. Medical Physics 2004, 31, 3242.
Smith, et al., Automatic detection of fiducial markers in fluoroscopy images for on-line calibration. Medical Physics 2005, 32, 1521.
Lee, et al., Prostate brachytherapy seed reconstruction with Gaussian blurring and optimal coverage cost. IEEE Transactions on Medical Imaging 2009, 28, 1955-1968.
Dehghan, et al., Brachytherapy seed reconstruction with joint-encoded C-arm single-axis rotation and motion compensation. Medical Image Analysis 2011, 15, 760-771.
Mitschke, et al., Recovering the X-ray projection geometry for three-dimensional tomographic reconstruction with additional sensors: Attached camera versus external navigation system. Medical Image Analysis 2003, 7, 65-78.
Noel, et al., Optimization of three-dimensional angiographic data obtained by self-calibration of multiview imaging. Medical Physics 2006, 33, 3901.
Kyriakou, et al., Simultaneous misalignment correction for approximate circular cone-beam computed tomography. Physics in Medicine and Biology 2008, 53, 6267-6289.
Panetta, et al., An optimization-based method for geometrical calibration in cone-beam CT without dedicated phantoms. Physics in Medicine and Biology 2008, 14, 3841-3861.
Parkinson, et al., Automatic alignment and reconstruction of images for soft X-ray tomography. Journal of Structural Biology 2012, 177, 259-266.
Wicklein, et al., Image features for misalignment correction in medical flat-detector CT. Medical Physics 2012, 39, 4918-4931.
Tran, et al., Robust registration of electron tomography projections without fiducial markers. IS&T/SPIE Electronic Imaging 2013, 86750.
Patel, et al., Self-calibration of a cone-beam micro-CT system. Medical Physics 2009, 36, 48.
Kingston, et al., Reliable automatic alignment of tomographic projection data by passive auto-focus. Medical Physics 2011, 38, 4934-4945.
Meng, et al., Online geometric calibration of cone-beam computed tomography for arbitrary imaging objects. IEEE Transactions on Medical Imaging 2013, 32, 278-288.
Prummer, et al., Multi-modal 2D-3D Non-rigid Registration. Medical Imaging 2006, 61440.
Tomazevic, et al., 3-D/2-D registration by integrating 2-D information in 3-D. IEEE Transactions on Medical Imaging 2006, 25, 17-27.
Zhang, et al., 3-D reconstruction of the spine from biplanar radiographs based on contour matching using the Hough transform. IEEE Transactions on Bio-Medical Engineering 2013, 60, 1954-1964.
Zheng, Statistical shape model-based reconstruction of a scaled, patient-specific surface model of the pelvis from a single standard AP x-ray radiograph. Medical Physics 2010, 37, 1424.
Moura, et al., A Flexible Approach for the Calibration of Biplanar Radiography of the Spine on Conventional Radiological Systems. CMES: Computer Modeling in Engineering and Sciences 2010, 60, 115-138.
Otake, et al., An Iterative Framework for Improving the Accuracy of Intraoperative Intensity-Based 2D/3D Registration for Image-Guided Orthopedic Surgery. Information Processing in Computer-Assisted Interventions 2010, 6135, 23-33.
Moura, et al., Fast 3D reconstruction of the spine from biplanar radiographs using a deformable articulated model. Medical Engineering and Physics 2011, 33, 924-933.
Schumann, et al., An integrated system for 3D hip joint reconstruction from 2D X-rays: a preliminary validation study. Annals of Biomedical Engineering 2013, 41, 2077-2087.
Otake, et al., 3D-2D Registration in Mobile Radiographs: A Tool for Safety Checks and QA of Surgical Product. Physics in Medicine and Biology 2014.
Otake, et al., Robust 3D-2D image registration: application to spine interventions and vertebral labeling in the presence of anatomical deformation. Physics in Medicine and Biology 2013, 58, 8535-8553.
Otake et al., Intraoperative image-based multiview 2D/3D registration for image-guided orthopaedic surgery: incorporation of fiducial-based C-arm tracking and GPU-acceleration. IEEE Transactions on Medical Imaging 2012, 31, 948-962.
Tornai, et al., Fast DRR generation for 2D to 3D registration on GPUs. Medical Physics 2012, 39, 4795-4799.
Uneri, et al., 3D-2D registration for surgical guidance: Effect of projection view angles on registration accuracy. Physics in Medicine and Biology 2014, 59. 271-287.
Schmidgunst, et al., Calibration model of a dual gain flat panel detector for 2D and 3D x-ray imaging. Medical Physics 2007, 34, 3649.
Feldkamp, et al., Practical cone-beam algorithm. Journal of the Optical Society of America A 1984, 1, 612-619.
Zhang, et al., Correction of motion artifacts in cone-beam CT using a patient-specific respiratory motion model. Medical Physics 2010, 37, 2901-2909.
Tang, et al., A fully four-dimensional, iterative motion estimation and compensation method for cardiac CT. Medical Physics 2012, 39, 4291-4305.

(56) References Cited

PUBLICATIONS

Brehm, et al., Artifact-resistant motion estimation with a patient-specific artifact model for motion-compensated cone-beam CT. Medical Physics 2013, 40, 101913.

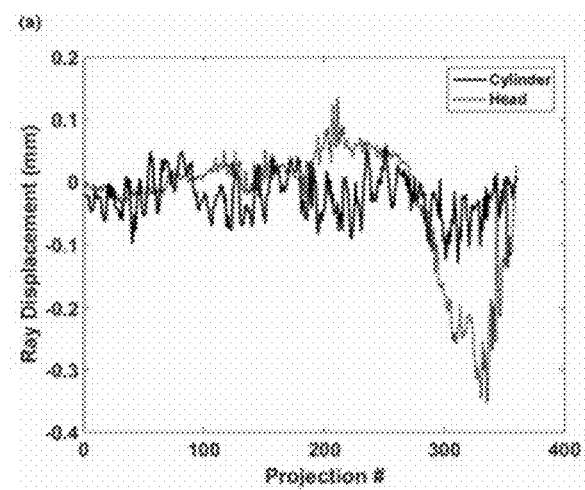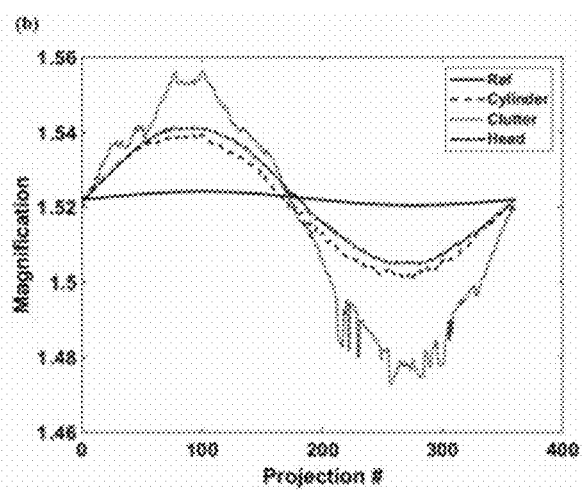
FIG. 8A   FIG. 8B

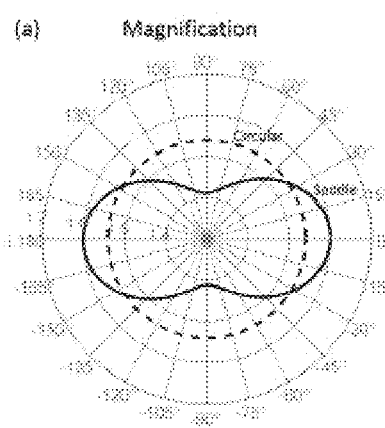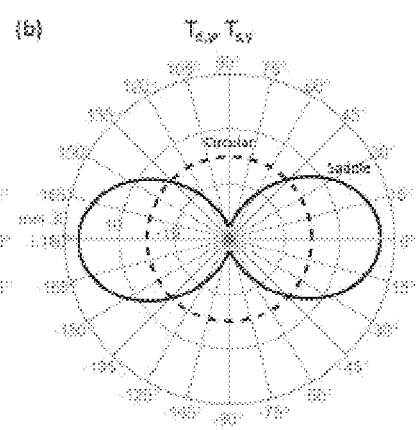
FIG. 14A  FIG. 14B

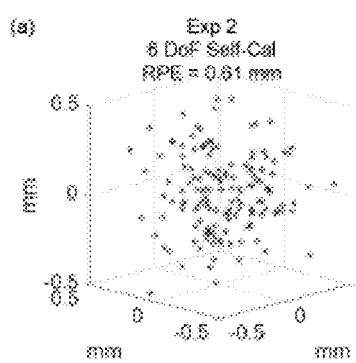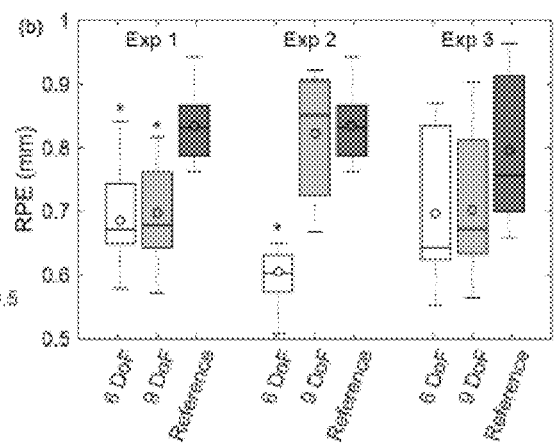
FIG. 17A  FIG. 17B

SELF-CALIBRATING PROJECTION GEOMETRY FOR VOLUMETRIC IMAGE RECONSTRUCTION

CROSS REFERENCE TO RELATED APPLICATIONS

This application claims the benefit of U.S. Provisional Patent Application No. 62/297,255 filed Feb. 19, 2016, which is incorporated by reference herein, in its entirety.

FIELD OF THE INVENTION

The present invention relates generally to medical imaging. More particularly, the present invention relates to a method for self-calibrating projection geometry for volumetric image reconstruction.

BACKGROUND OF THE INVENTION

Tomographic imaging systems such as diagnostic CT scanners, tomosynthesis systems, and cone-beam CT (CBCT) systems require a known system geometry in order to perform accurate image reconstruction. Because image quality can be sensitive to sub-mm errors in geometry and system geometry can change over time, most CT/CBCT systems employ some form of routine (e.g., daily) geometric calibration to provide up-to-date system geometry for each patient acquisition. However, errors in geometric calibration persist, resulting in blurry images, ring artifacts, geometric distortion, and other artifacts. Reasons for such errors include overly simplistic models of system geometry, change introduced to the system (whether intentional or unintentional), scan-to-scan variability such as system jitter, and non-reproducible orbits such as custom-designed trajectories. Additionally, (rigid) patient motion can be corrected by updating the system geometry on a per-projection basis to effectively move the system with respect to the virtually fixated patient. Therefore, a method for providing an accurate scan-specific geometric description of the acquired projections would be highly desired.

System geometry for each projection in a CT/CBCT acquisition can be divided into two sets of parameters—intrinsic and extrinsic. Intrinsic parameters define the x-ray source position relative to the x-ray detector and can be parameterized by 3 degrees of freedom (DOF). Most CT/CBCT systems have fixed intrinsic geometry, including diagnostic CT scanners, dedicated dental, extremity, and head CBCT scanners, and some mobile C-arms, as illustrated in FIG. 1. FIG. 1 also illustrates a robotic C-arm with adjustable geometry and a variable orbit. Extrinsic parameters relate the imaging system pose to the patient reference frame and are represented by a 6-DOF translation and rotation (or equivalently, 6-DOF patient pose relative to the detector coordinate frame). Calibrating the projection geometry for fixed-geometry systems is inherently a 6-DOF problem (per projection) given that the intrinsic parameters are constrained and can be well-calibrated; however, the intrinsics are known to vary from scan to scan for reasons including gravity-induced flex and system jitter. A full 9-DOF calibration that jointly estimates the extrinsic and intrinsic parameters (per projection) would address the issue of unknown intrinsics, including for adjustable-geometry systems. Once the 9 DOFs (per projection) are known, the system geometry can then be represented by a set of projection matrices (PMs)—one PM per projection.

A number of "conventional" geometric calibration methods exist for tomographic systems that estimate the geometry of each projection using a prior calibration scan and then used for image reconstruction. For example, in CBCT, methods include the use of a specially designed calibration phantom, such as a spiral BB phantom, a phantom with two rings of BBs, or other patterns of markers. However, there may be a change in geometry or other inconsistencies between the previously acquired geometric calibration scan and the current patient scan, or the geometry/trajectory may be irreproducible altogether (e.g., custom-designed trajectories on the Zeego). Scan-specific ("on-line") geometric calibration methods have been proposed that simultaneously acquire fiducial markers with the patient scan; however, this requires placing markers on or next to the patient and within the imaging field of view, which is a cumbersome (and sometimes impossible) process that superimposes markers onto the projections and is detrimental to image reconstruction, or are limited to niche applications where small high-contrast objects are already within the patient (e.g., brachytherapy). Other scan-specific methods propose the use of additional sensors to capture the source and detector positions, but introduce additional hardware and workflow complexity. Image-based "auto-focus" methods require time-consuming reconstructions in each function evaluation and/or optimize image quality metrics over a set of few simple parameters that describe the overall geometry of the system (e.g., assuming a circular orbit), rather than the full geometry of each projection.

In many applications of CT/CBCT systems that require geometric calibration (e.g., intraoperative CBCT), a 3D volumetric representation of the patient (e.g., preoperative CT) is often available. In this case, the patient himself can be used as a fiducial, which obviates the need for external fiducials or trackers that are often inaccurate and a burden to workflow. In this concept of "patient as the fiducial," the feature-rich anatomy of a patient can be used by a 3D-2D registration process to provide "self-calibrated" geometry, given that some of the anatomy is known ahead of time (e.g., preoperative CT). Despite the desire for shared anatomical structures between the current scan and the prior scan, the current scan is still needed for providing up-to-date visualization in applications including targeting soft-tissue structures (e.g., tumors), monitoring anatomical change (e.g., bleeds, tumor resection), and/or verifying interventional device placement (e.g., stents, coils, pedicle screws), and the self-calibration should be robust against any such changes. Previously proposed 3D-2D registration methods required several projections to perform a 3D-3D registration between the preoperative CT and reconstruction from sparse projections and required a known geometric calibration. Registration of a prior 3D volume to individual 2D projections (e.g., radiographs) has also been previously proposed, but required prior calibration, approximate geometric knowledge, or imaging the patient with an additional calibration fiducial of known shape.

Existing geometric calibration for tomographic systems, includes calibration performed "off-line" with dedicated phantoms (generally containing small, high-contrast markers such as BBs in known locations), calibration performed "on-line" with a known fiducial marker placed into the imaging field of view and acquired simultaneously with the patient, and "auto-focus" methods that adjust geometric parameters to improve image quality. However, none can provide a complete, scan-specific description of the system geometry without introducing additional workflow complexities that can be cumbersome (and sometimes impossible) to use. For example, the "off-line" calibration methods cannot be used for non-reproducible trajectories, nor can they account for scan-to-scan variability such as system jitter. The "on-line" calibration methods require use of additional markers or hardware that interferes with workflow and often with image reconstruction. Lastly, the "auto-focus" methods do not provide a complete geometric description and instead usually only tune a few parameters due to the computational challenges associated with tuning all available parameters.

Accordingly, there is a need in the art for a method of self-calibrating projection geometry for volumetric image reconstruction.

SUMMARY OF THE INVENTION

The foregoing needs are met, to a great extent, by the present invention which provides a method for self-calibrating projection geometry for a volumetric image reconstruction including selecting a prior volumetric representation of the patient. The method includes dividing a cone-beam computed tomography CBCT scan into a number of projections and selecting a projection from the number of projections. The method also includes applying a 9-degree-of-freedom geometric calibration of the selected projection. Additionally the method includes generating a projection matrix from the 9-degree-of-freedom geometric calibration of the selected projection and generating a three-dimensional, volumetric reconstruction of the CBCT scan using a plurality of the projection matrices.

In accordance with an aspect of the present invention, a preoperative CT is used as the prior volumetric representation of the patient. The CMA-ES optimization algorithm is used for solving a 9-degree-of-freedom geometric calibration of the selected projection. The NGI similarity metric can also be used for applying a 9-degree-of-freedom geometric calibration of the selected projection. The method includes applying fixed intrinsic parameters such that the 9-degree-of-freedom geometric calibration is limited to a 6-degree-of-freedom geometric calibration. The method includes initializing the 9-degree-of-freedom geometric calibration of the selected projection with the 9-degree-of-freedom geometric calibration result of another projection. The cone-beam computed tomography CBCT scan can in some embodiments take the form of a tomosynthesis scan and the volumetric reconstruction of the CBCT scan is instead a volumetric reconstruction of the tomosynthesis scan.

In accordance with another aspect of the present invention, the 9-degree-of-freedom, self-calibration is repeated for each of the projection of the number of projections. A Feldkamp-Davis-Kress (FDK) three-dimensional, volumetric reconstruction is performed or alternately a model-based image reconstruction (MBIR) three-dimensional, volumetric reconstruction is performed. Any other suitable form of reconstruction known to or conceivable by one of skill in the art could also be used. A non-transitory computer readable medium is programmed for executing steps of the method. The method can also include estimating intrinsic parameters of the selected projection using the 9-degree-of-freedom geometric calibration.

In accordance with still another aspect of the present invention, a system for self-calibrating projection geometry for a volumetric image reconstruction of a subject includes a cone-beam computed tomography (CBCT) scanner for generating CBCT image data for the subject. The system includes a non-transitory computer readable medium programmed for selecting a prior volumetric representation of the subject. The non-transitory computer readable medium is programmed for dividing a cone-beam computed tomography (CBCT) scan into a number of projections, selecting a projection from the number of projections, and applying a 9-degree-of-freedom geometric calibration of the selected projection. Further, the non-transitory computer readable medium is programmed for generating a projection matrix from the 9-degree-of-freedom geometric calibration of the selected projection and generating and displaying a three-dimensional, volumetric reconstruction of the CBCT scan using a plurality of the projection matrices.

In accordance with yet another aspect of the present invention, the system uses a preoperative CT as the prior volumetric representation of the patient. A CMA-ES optimization algorithm can be used for applying a 9-degree-of-freedom geometric calibration of the selected projection. An NGI similarity metric can be used for applying a 9-degree-of-freedom geometric calibration of the selected projection. The non-transitory computer readable medium is programmed for applying fixed intrinsic parameters such that the 9-degree-of-freedom geometric calibration is limited to a 6-degree-of-freedom geometric calibration. The 9-degree-of-freedom geometric calibration of the selected projection is initialized with the 9-degree-of-freedom geometric calibration result of another projection. The cone-beam computed tomography CBCT scan takes the form of a tomosynthesis scan and the volumetric reconstruction of the CBCT scan is instead a volumetric reconstruction of the tomosynthesis scan. The 9-degree-of-freedom, self-calibration is repeated for each of the projection of the number of projections.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 8A and 8B illustrate graphical views of the difference in perpendicular ray placement between true geometry and geometry found using 3D-2D registration and magnification of the system for each projection respectively.

FIGS. 14A and 14B are graphical views of the saddle orbit for Experiment 4.

FIGS. 17A and 17B illustrate graphical views that summarize the results for the four experiments in terms of the RPE, echoing the results of FIGS. 16A-16L.

DETAILED DESCRIPTION

Figure 1:
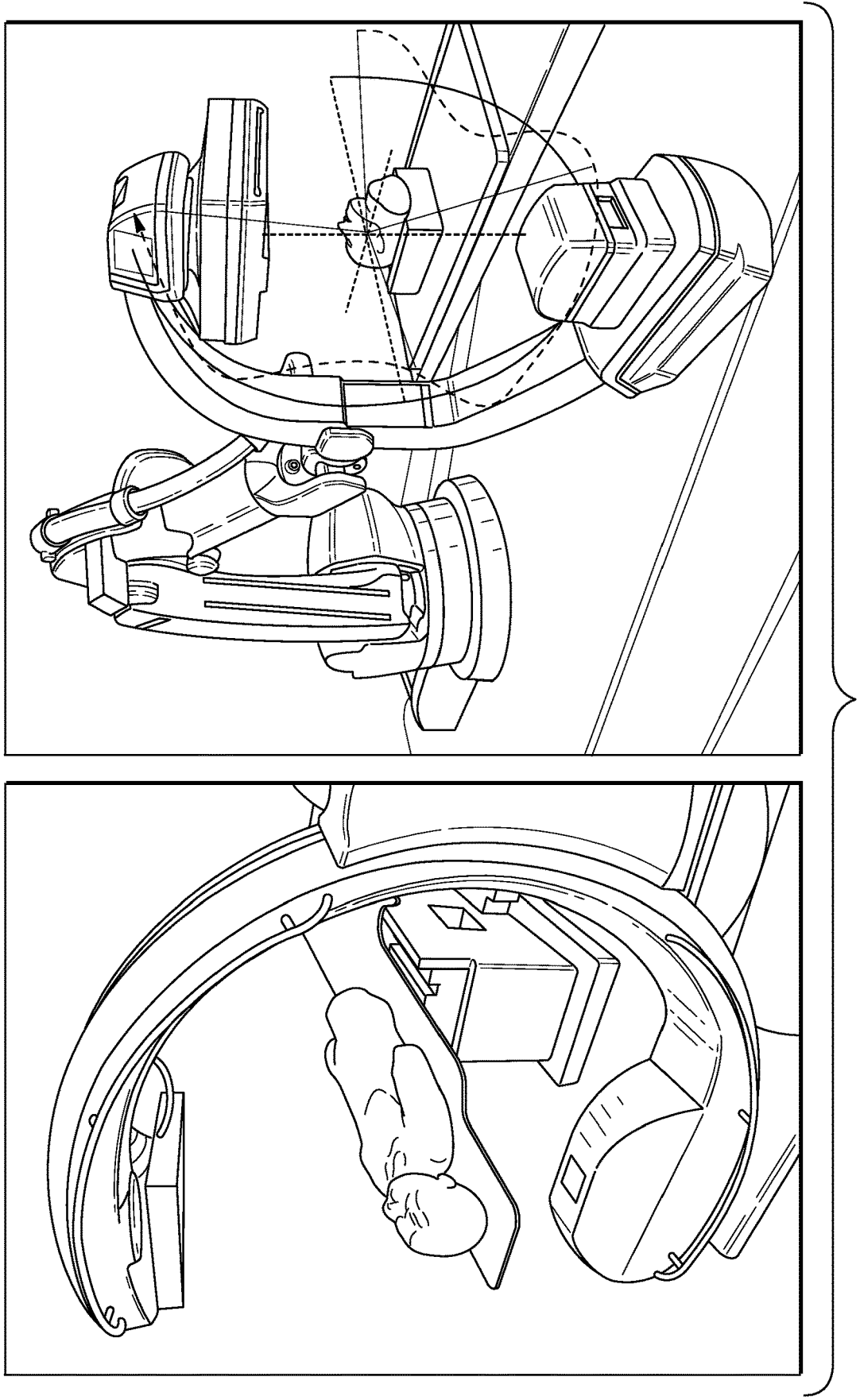
FIG. 1 illustrates a fixed-geometry mobile C-arm and also a robotic C-arm with a variable orbit.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method for enabling volumetric image reconstruction from unknown projection geometry of tomographic imaging systems, including CT, cone-beam CT (CBCT), and tomosynthesis systems. The invention enables image reconstruction in cases where it was not previously possible (e.g., custom-designed trajectories on robotic C-arms, or systems using uncalibrated geometries), and more broadly offers improved image quality (e.g., improved spatial resolution and reduced streak artifact) and robustness to patient motion (e.g., inherent compensation for rigid motion) in a manner that does not alter the patient setup or imaging workflow for practitioners. The method provides a means for accurately estimating the complete geometric description of each projection acquired during a scan by simulating various poses of the x-ray source and detector to determine their unique, scan-specific positions relative to the patient, which is often unknown or inexactly known (e.g., a custom-designed trajectory, or scan-to-scan variability in source and detector position). An image registration framework is used that only requires knowledge of the patient (e.g., prior volumetric image such as a diagnostic CT) and avoids additional workflow complexities by operating independently of fiducial markers or extra hardware. The invention was demonstrated for a C-arm CBCT system and shown to substantially improve image quality over conventional geometric calibration methods.

The present invention is unique in that it uses the patient anatomy itself as the fiducial to provide highly accurate self-calibrated projection geometry, and is capable of doing so from commonly available volumetric images of a patient, such as a diagnostic CT. The method leverages a 3D-2D image registration framework to determine the complete geometric description of each acquired projection. The resulting self-calibrated geometry can then be used to perform tomographic image reconstruction with precisely known geometry, eliminating artifacts resulting from unknown geometry or patient motion, including image blur, geometric distortion, streak artifact, and motion artifact. Examples of systems that would benefit from such technology include C-arm CBCT systems, which are often prone to change in geometry over time; robotic C-arms capable of customizable trajectories; and CT scanners and dedicated CBCT systems, whose image quality can still be sensitive to small geometric errors and patient motion.

Further, the present invention is directed to a self-calibrating geometry method that utilizes a 3D-2D registration framework. In particular, the algorithm leverages rigid, high-contrast anatomy (e.g., skull, spine, or other bone) to simultaneously seek all 9-DOF geometric parameters that maximize similarity between an acquired 2D projection and digitally reconstructed radiographs (DRRs) of the 3D volume. This is done for each projection of the CBCT acquisition, and the resulting projection geometry (represented by a set of PMs) is then used to perform image reconstruction and evaluated for geometric calibration accuracy. The self-calibrating geometry leverages 3D-2D registration framework to estimate the scan-specific PMs of each acquisition. Key to the method is a robust optimization facilitated by performing a large number of function evaluations in an efficiently parallelized GPU implementation.

Figure 2:
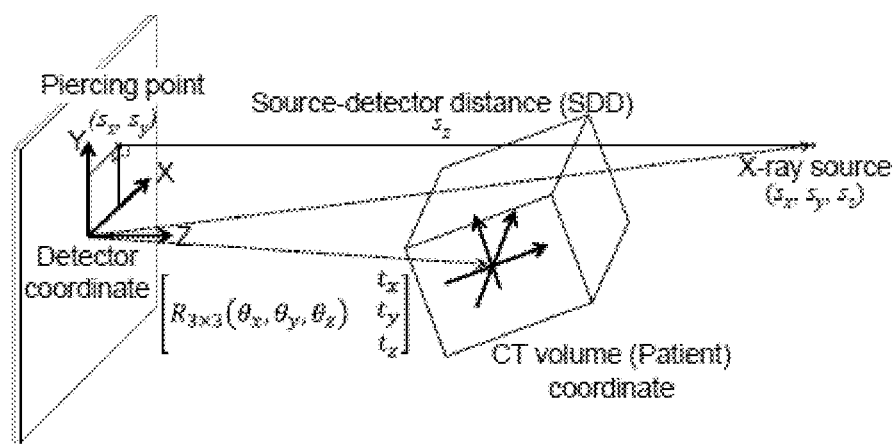
FIG. 2 illustrates a schematic view of a projection geometry and the parameters associated with the source, CT, and detector coordinate frames.

The projection geometry for a single projection is illustrated in FIG. 2. FIG. 2 illustrates a schematic view of a projection geometry and the parameter associated with the source, CT, and detector coordinate frames. The world coordinate frame is located at the center of the detector with the X and Y axes parallel to the detector edge and the Z-axis formed by their cross product. The coordinate frame of the CT volume was defined at the center of the volume, and its position and orientation with respect the world coordinate frame ("extrinsic" parameters) was represented as a 6-element vector of translations and rotations ($t_x, t_y, t_z, \theta_x, \theta_y, \theta_z$). The projection geometry was parameterized by the source position ($s_x, s_y, s_z$) with respect to the world coordinate ("intrinsic" parameters), where $s_z$ represents the length of the perpendicular line from the source to the detector (source-to-detector distance, SDD) and ($s_x, s_y$) represents the detector piercing point. These nine parameters uniquely represent the following PM relating a 3D point and its projection in the 2D detector plane:

$$\begin{pmatrix} u \\ v \end{pmatrix} \sim P \begin{pmatrix} x \\ y \\ z \\ 1 \end{pmatrix} = \begin{pmatrix} s_z & 0 & s_x & 0 \\ 0 & s_z & s_y & 0 \\ 0 & 0 & 1 & 0 \end{pmatrix} \begin{pmatrix} R_{3\times3}(\theta_x, \theta_y, \theta_z) & \begin{matrix} t_x - s_x \\ t_y - s_y \\ t_z - s_z \end{matrix} \\ 0\ 0\ 0 & 1 \end{pmatrix} \begin{pmatrix} x \\ y \\ z \\ 1 \end{pmatrix} \quad (1)$$

where $(x, y, z)^T$ is the 3D point in the CT coordinate frame, $(u, v)^T$ is the projected location in the detector coordinate frame, $R_{3\times3}$ is the rotation matrix for the CT frame with respect to the detector frame parameterized by $(\theta_x, \theta_y, \theta_z)$, P is a 3×4 PM, and the ~ symbol denotes that the left and right sides are equal to within scalar multiplication—i.e., $(a\ b)^T \sim (A\ B\ C)^T$ implying $a=A/C$ and $b=B/C$.

Figure 3:
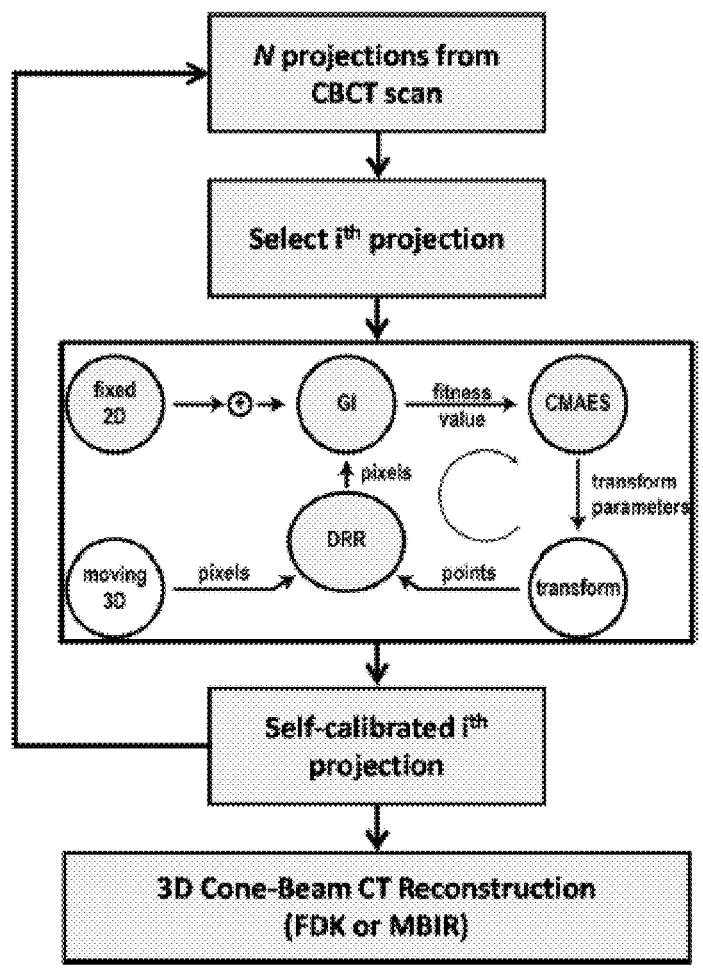
FIG. 3 illustrates a flow diagram for geometric calibration using a 3D-2D registration framework per projection.

The framework illustrated in FIG. 3 and underlying the 3D-2D registration method uses an optimization algorithm to seek model parameters that maximize similarity between the projection (fixed 2D image) and DRR (of the moving 3D volume)—extended to a 9-DOF representation of projection geometry that provides a scan-specific geometric calibration of the imaging system. FIG. 3 illustrates a flow diagram for geometric calibration using a 3D-2D registration framework per projection. The self-calibration from other projections (e.g., neighboring projections) can be used to inform the initial estimate and/or constrain the search space of the current projection being calibrated. Once the geometry is estimated for all N projections, the CBCT images can be reconstructed using any desired method including FDK or MBIR. The optimization algorithm was implemented on CPU for flexibility in parameter selection. DRRs and the similarity metric were computed on GPU, to drastically improve computational performance.

Normalized gradient information (NGI) was used as a similarity metric. The metric compares the gradient magnitude at each pixel and ignores gradients appearing only in one of the images, thus providing robustness to inconsistencies between the projection image and DRR, e.g., due to foreign objects such as tools and devices, deformation, or other changes in anatomy.

Conventional geometric calibration was used to provide a well-approximated initialization for the optimization in a C-arm with fixed geometry. In the case of adjustable-geometry systems, initialization of the first projection could be provided by some basic input from the user/system (e.g., PA or LAT view, approximate source-detector distance), and subsequent projections could be initialized by the estimated geometry of the previous projection in a bootstrapping manner.

The covariance matrix adaptation-evolutionary strategy (CMA-ES) was used to solve the optimization problem:

$$\hat{s}_x, \hat{s}_y, \hat{s}_z, \hat{t}_x, \hat{t}_y, \hat{t}_z, \hat{\theta}_x, \hat{\theta}_y, \hat{\theta}_z = \underset{s_x,s_y,s_z,t_x,t_y,t_z,\theta_x,\theta_y,\theta_z \in S}{\operatorname{argmax}} NGI(I_v I_o(s_x, s_y, s_z, t_x, t_y, t_z, \theta_x, \theta_y, \theta_z)) \quad (2)$$

where S represents the boundary of the solution space (i.e., search range). CMA-ES calculations were performed on CPU in Matlab (The Mathworks, Natick, Mass.) with function calls to an externally compiled C++ library for computing DRRs and similarity metric on GPU using CUDA (nVidia, Santa Clara Calif.).

CMA-ES generates multiple sample solutions (population size $\lambda$) in each generation to be independently evaluated, allowing parallelization of $\lambda$ function evaluations. In each generation, $\lambda$ PMs were computed based on the nine parameters at the sample solutions in the current generation using equation (1), with DRRs and the similarity metric for $\lambda$ samples simultaneously computed on the GPU.

Conventional geometric calibration provides a PM $P_i$ for each projection, indexed by i, with respect to a CBCT "world" frame. The 6-DOF geometric calibration assumes known intrinsic parameters (e.g., from the conventional calibration) while estimating the extrinsic parameters by using 3D-2D registration to find a rigid volume transform (4×4 matrix representing translation and rotation) $T_{CBCT}^{CT^*}$ that best matches the acquired projection with DRRs of the CT volume. The transformation is used to update the PM:

$$\tilde{P}_i = P_i T_{CBCT}^{CT,i}(T_{CBCT}^{CT^*})^{-1}, \quad (3)$$

where $T_{CBCT}^{CT^*}$ represents a common transform between the CT volume and CBCT frame (e.g., some "average" transform), but in practice any common transform such as $T_{CBCT}^{CT,1}$ (estimated transform from the first projection) or the estimated transform from 3D-2D registration of a set of projections (e.g., 10 evenly spaced projections) can be used.

The 9-DOF geometric calibration additionally estimates the intrinsic parameters of each projection, providing an updated estimate for $P_i$ as well. Experiments were conducted with an anthropomorphic head phantom (The Phantom Laboratory, Greenwich, N.Y.), which contained an intracranial space filled with iodinated gelatin (~50 HU), simulated ventricles carved from iodinated candle wax (~0 HU), and acrylic spheres of varying diameter (~100 HU). A CT scan (SOMATOM Definition Flash, Siemens Healthcare) was acquired at 120 kVp, 500 mAs and reconstructed with the H60s kernel and 0.5×0.5×0.6 mm³ voxels for use as the ("preoperative") 3D volume. These experiments are not meant to be considered limiting and are included merely by way of example. Any implementation known to or conceivable by one of skill in the art could be used.

"Intraoperative" CBCT scans were performed with a prototype mobile C-arm (modified Powermobil, Siemens Healthcare) at 100 kVp, 320 mAs (total), acquiring 198 projections over an approximately semicircular orbit. The C-arm was equipped with a flat-panel detector (PaxScan 3030+, Varian Medical Systems, Palo Alto, Calif.) operated in dual-gain mode and 2×2 binning (effective pixel size 0.388×0.388 mm²) with a nominal fixed geometry of 600 mm source-axis distance (SAD) and 1200 mm source-detector distance (SDD). Conventional geometric calibration was performed prior to scanning using a spiral BB phantom.

A deep brain stimulation (DBS) electrode (Model 3387, Medtronic, Minneapolis, Minn.) was inserted into the cranial space of the phantom to simulate an image-guided neurosurgical procedure. The high density and high atomic number of the thin metal leads and electrodes (platinum/iridium alloy) and thin tungsten stylet were particularly useful for assessing geometric calibration errors due to high sensitivity to such errors, which produced easily visualized streaks emanating from the edge of the device. The phantom was scanned twice, with the DBS electrode placed in slightly different locations between the two scans. Parameters for CMA-ES optimization include $\lambda$=50, initialization provided by the conventional geometric calibration, and $\sigma$=(10 mm, 10 mm, 10 mm, 10 mm, 10 mm, 10 mm, 1°, 1°, 1°). No downsampling was applied to the CT volume, while downsampling by a factor of 2 was applied to the projections to better match the voxel size. Each projection was independently self-calibrated using both 6-DOF and 9-DOF 3D-2D registration.

Figure 4A:
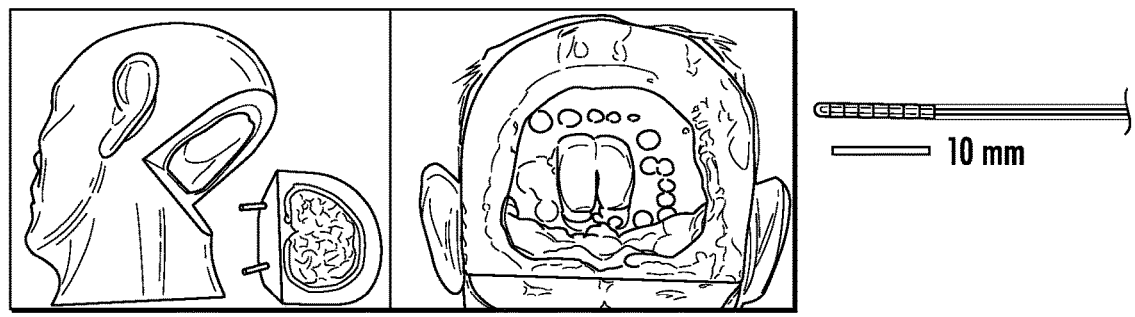
FIG. 4A illustrates an anthropomorphic head phantom and DBS electrode.
Figure 4B:
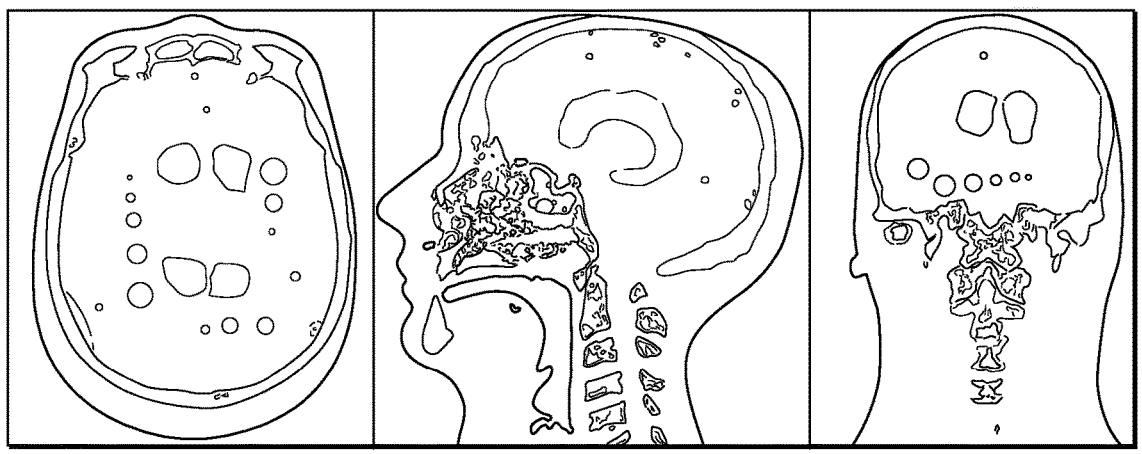
FIG. 4B illustrates CT volume: axial, sagittal, and coronal planes.
Figure 4C:
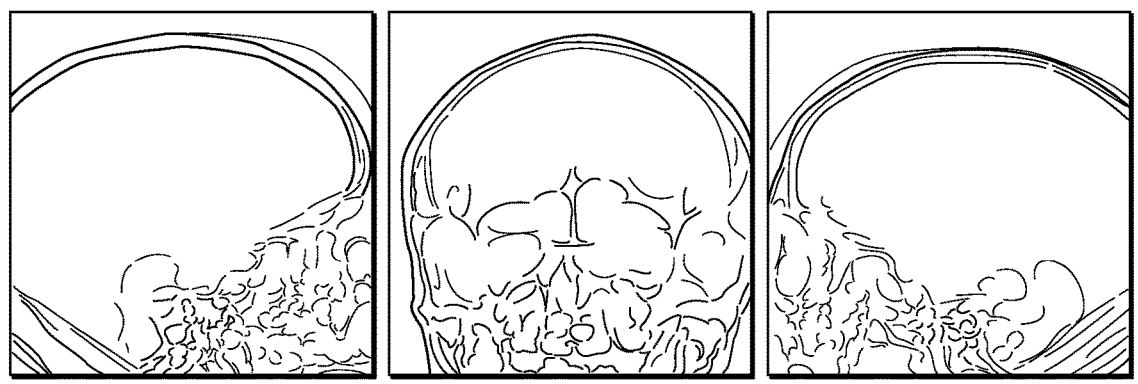
FIG. 4C illustrates CBCT projections acquired at 0, 90, and 180 degrees.

Image reconstruction was performed with a modified FDK algorithm (i.e., filtered backprojection, FBP), where the backprojection geometry for each projection was defined using PMs. Reconstructed image quality from conventional geometric calibration, 6-DOF self-calibration, and 9-DOF self-calibration were compared by assessing streak artifact levels. FIGS. 4A-4C illustrates image views of the experimental setup. FIG. 4A illustrates an anthropomorphic head phantom and DBS electrode. FIG. 4B illustrates CT volume: axial, sagittal, and coronal planes, and FIG. 4C illustrates CBCT projection images 1, 100, and 198.

Figures 5A, 5B:
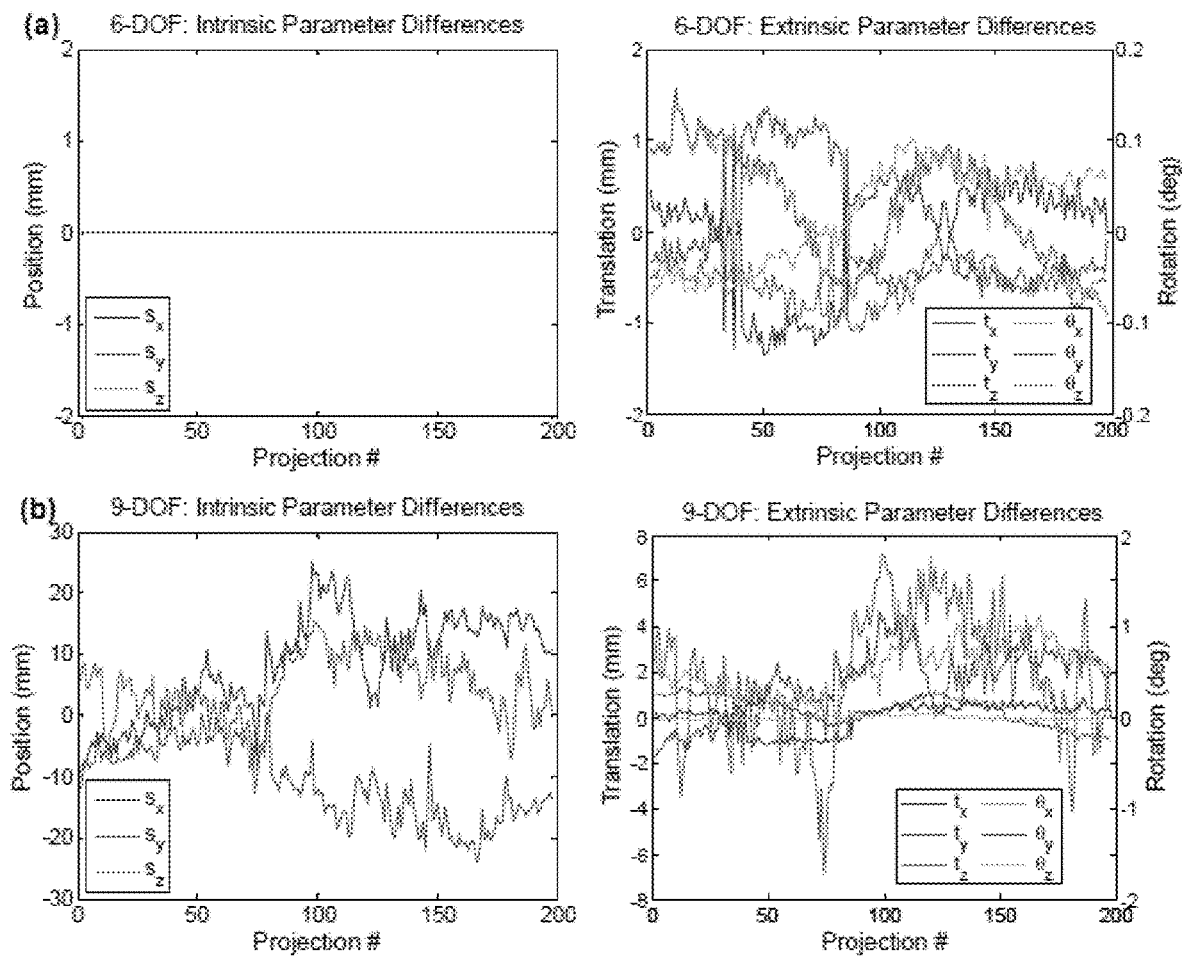
FIG. 5A illustrates a variation across projections between 6-DOF registration parameters and conventional geometric calibration.
FIG. 5B illustrates a variation across projections between 9-DOF registration parameters and conventional geometric calibration.

The self-calibration PMs were compared to those of the conventional geometric calibration by plotting the difference in the nine parameters for all projections of the first scan of the phantom, as illustrated in FIGS. 5A and 5B. FIGS. 5A and 5B illustrate graphical views of registration results for all projections (scan 1). FIG. 5A illustrates a difference between 6-DOF registration parameters and conventional geometric calibration. The intrinsic parameters (source position $s_x$, $s_y$, $s_z$) were held fixed, so only the extrinsic parameters (translation $t_x$, $t_y$, $t_z$ and rotation $\theta_x$, $\theta_y$, $\theta_z$) were updated. FIG. 5B illustrates the difference between 9-DOF registration parameters and conventional geometric calibration. The 6-DOF self-calibration uses the same intrinsic parameters as the conventional geometric calibration (hence, no difference), while using the extrinsic parameters to compensate for any geometric errors, including jitter and other non-reproducibility in the source-detector geometry. In addition to some low frequency corrections, there are also view-to-view corrections up to ~1 mm in translation and ~0.1° in rotation at the object.

On the other hand, the 9-DOF self-calibration demonstrates large variation in the intrinsic parameters, with the source position varying from the conventional geometric calibration by up to ~20 mm. The extrinsic parameters also exhibit larger differences—up to ~8 mm in translation and ~1° in rotation at the object.

Figure 6:
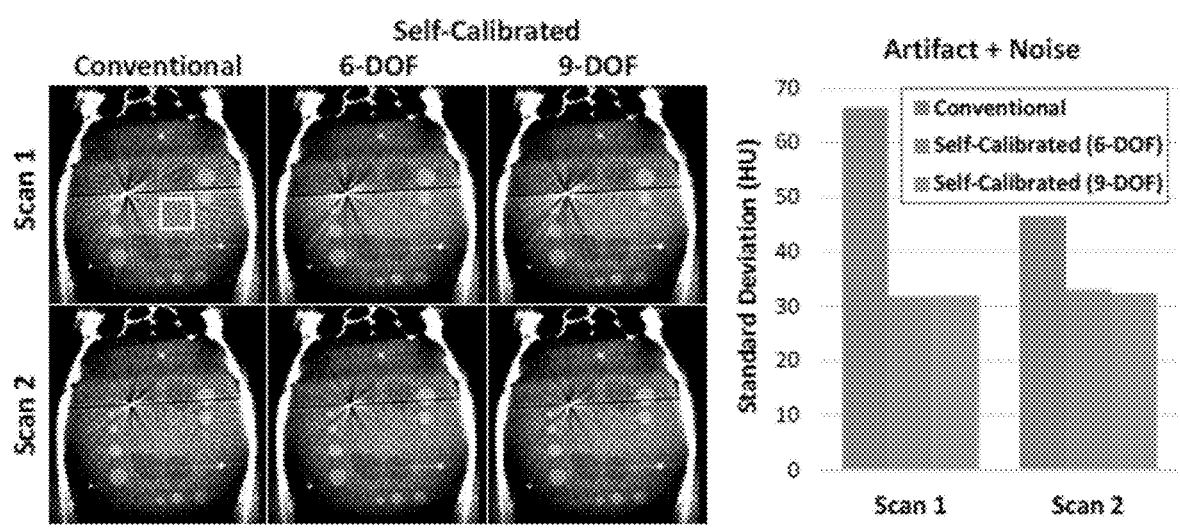
FIG. 6 illustrates image and graphical views of CBCT image reconstruction results.

Axial slices of the resulting image reconstructions are shown in FIG. 6 for the two scans acquired of the phantom. Reconstruction with conventional geometric calibration yields strong streak artifact off of the thin, high-contrast DBS electrode that are no longer present in the reconstructions using 6-DOF or 9-DOF self-calibrated geometries. The remaining artifact is due to standard metal artifact such as beam hardening and sampling (e.g., incomplete orbit and streak along start/stop projections) and is unrelated to geometric calibration error. Thus, although conventional geometric calibration demonstrated that the orbit was largely reproducible (producing reasonable reconstruction of soft-tissue structures and bone), small geometric errors due to minor changes in the geometry such as jitter contribute to degradation of image quality. The standard deviation in a uniform region of the phantom was used as a metric for the combined artifact and noise level, showing that the self-calibrated geometry was less susceptible to artifact (producing consistent levels of noise ~31 HU), while conventional geometric calibration is prone to large (and inconsistent) artifact levels that can confound the imaging task. FIG. 6 illustrates image and graphical views of CBCT image reconstruction results. Conventional geometric calibration exhibits streak artifact emanating from the DBS electrode in two separate scans (1 and 2) due to errors in the assumed geometry. Both 6-DOF and 9-DOF self-calibration greatly reduce the streak artifact, although other metal artifact (unrelated to geometric calibration errors) remains. The standard deviation of the yellow region was used to measure the combined artifact and noise level, with self-calibration showing consistent levels of noise (~31 HU), while conventional calibration is susceptible to large artifact levels.

The experimental results demonstrate the feasibility of using the patient as a fiducial for self-calibrating geometry that leverages a volumetric representation of the patient (e.g., preoperative CT) to estimate the geometric parameters (and PM) most consistent with each acquired projection. The self-calibrated geometry is then used to perform accurate CBCT image reconstruction, compensating for unknown geometry, geometric errors, and/or patient motion. While 6-DOF self-calibration worked fairly well for the mobile C-arm (which has an approximately fixed intrinsic geometry that was estimated by conventional geometric calibration), a 9-DOF self-calibration is essential for systems with adjustable or unknown intrinsic geometry (e.g., Zeego). Moreover, in non-reproducible geometries and trajectories (such as custom-designed trajectories), self-calibration is critical because conventional geometric calibration is completely unavailable. Additionally, self-calibration can account for (rigid) patient motion, because it estimates the patient position relative to the imaging system and does not require complex deformation fields of patient motion used in motion-compensated reconstruction, which are performed with reconstructed images that suffer streak artifact due to angular undersampling and motion. Without self-calibration, the reconstruction is susceptible to (rigid) patient motion (e.g., blurry image or other motion artifact), system jitter (e.g., streaks from high-contrast objects), and/or complete inability to perform meaningful reconstruction (e.g., custom-designed trajectories where the geometry is otherwise unknown).

Because accurate reconstruction is dependent on knowledge of the projection geometry, fast implementation of self-calibration is important for fast reconstructions. The GPU-accelerated CMA-ES optimization in this work required ~5 sec per projection for 6-DOF and ~17 sec per projection for 9-DOF registration on a single mid-end GPU (GTX 580, Nvidia, Santa Clara, Calif.). The self-calibration could be made faster with good initialization (e.g., bootstrapping from the previous projection), faster GPUs (e.g., GTX Titan), multiple GPUs (e.g., each processing a subset of the projections), and by trading off optimization robustness with speed (e.g., convergence criteria, population size, number of iterations) in a manner that still provides a sufficiently accurate reconstruction. Future work will consider using the CBCT projections to provide the 3D volume, where the geometry used for the preliminary CBCT reconstruction is assumed, roughly estimated, and/or from a previously calibrated geometry. This approach can be applied iteratively to bootstrap accuracy of both geometric calibration and image reconstruction.

In another implementation of the present method, normalized gradient information (NGI) was used as a similarity metric. This metric assesses the gradient magnitude at each pixel location and ignores strong gradients appearing in only one of the projection images, which provides robustness to inconsistencies between the projection image and the DRR. The NGI is the gradient information of the moving and fixed images, normalized to that of the moving image itself:

$$NGI(I_1, I_0) = \frac{GI(I_1, I_0)}{GI(I_0, I_0)} \quad (2)$$

where GI is the gradient information defined as:

$$GI(p_1, p_2) = \Sigma_{i,j \in \Omega} m(i,j) w(i,j) \min(|\nabla p_1(i,j)|, |\nabla p_2(i,j)|), \quad (3)$$

The min operator is used to ignore mismatching gradients by weighting only those gradients that are present in both images. Mismatching gradients can occur due to surgical tools in the field of view, deformations, or image artifacts. $\nabla p$ is a gradient vector where the gradient notation indicates the change in pixel value along the i and j directions at pixel location (i, j) within the image:

$$\nabla p(i, j) \triangleq \left( \frac{d}{di} p(i, j), \frac{d}{dj} p(i, j) \right). \quad (4)$$

The weighting term w was defined as:

$$w(i, j) = \frac{a_{i,j} + 1}{2} \quad (5)$$

$$a_{i,j} = \frac{\nabla p_1(i, j) \cdot \nabla p_2(i, j)}{|\nabla p_1(i, j)| |\nabla p_2(i, j)|} \quad (6)$$

where $a_{i,j}$ represents the cosine between gradient vectors at location (i, j). Alternative similarity measures include gradient correlation (GC), but NGI was found to be the most robust against mismatch and noise in the application of 3D-2D registration of images with comparable intensity scales.

Additional perturbations that would describe changes in system geometry of a realistic C-arm system (i.e. gravitational flex, system jitter, etc.) were added to a previously obtained geometric calibration and this perturbed geometry was used to provide an initialization for the self-calibration. Systematic perturbations were introduced by adding a constant value (δ) to the measured 9 DOF and random perturbations were introduced by adding a Gaussian distributed random variable with zero-mean and variance (σ). The perturbations were δ=σ=10 mm for $s_x$, $s_y$, $t_x$, $t_y$, δ=σ=4 mm for $s_z$, $t_z$, and δ=σ=4° for $\theta_x$, $\theta_y$, $\theta_z$. The 2D projections images were each downsampled by a factor of 3 and the 3D volume was downsampled by a factor of 2. This downsampling of the images helped to smooth noise and small gradients in the images that may negatively affect the registration while maintaining enough detail to register the images to the desired accuracy.

The covariance matrix adaptation-evolutionary strategy (CMA-ES) was chosen to solve the optimization problem:

$$\hat{s}, \hat{t}, \hat{\theta} = \underset{x,t,\theta \in S}{\mathrm{argmax}} NGI(I_1, I_0(x, t, \theta)), \quad (7)$$

where S represents the search range.

CMA-ES generates populations of sample points with each iteration and adjusts the mean and covariance matrix of the sample points according to the optimization problem to create a new generation. This repeats until convergence. Population size (λ) is therefore an adjustable parameter within the optimization framework. Choosing λ is a tradeoff in computation speed and robustness against false optima. For this work, the population size was chosen to be 100 for all projections to emphasize accuracy of the registration.

The stopping criterion for the CMA-ES algorithm was defined in terms of diminishing change in each of the 9-DOF parameters describing the pose of the object in CT coordinate space. For this application, a high level of accuracy was needed to determine the pose of the object to less than half the pixel size. With a typical detector pixel pitch on the order of 0.2 mm, the algorithm was run for a number of iterations required to find the object pose to within 0.1 mm. To be well within the desired accuracy tolerance for this preliminary work, the stopping criterion was chosen to be 0.01 mm for change in translations, and 0.01 degrees for rotations.

Figure 7A:
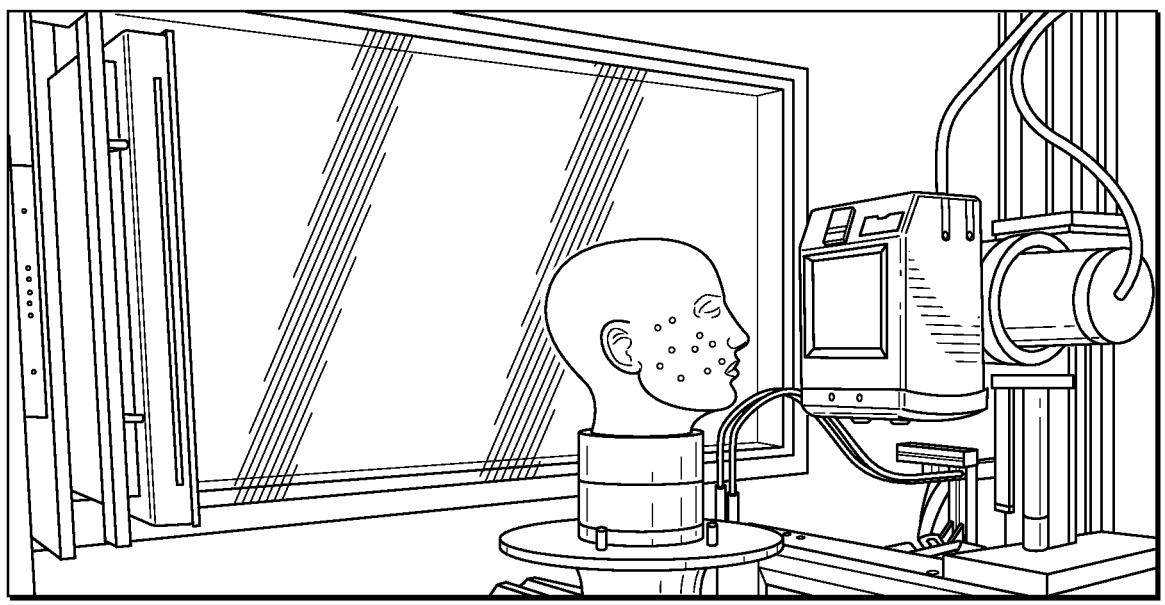
FIGS. 7A and 7B illustrate image views of the phantoms for the experimentation.
Figure 7B:
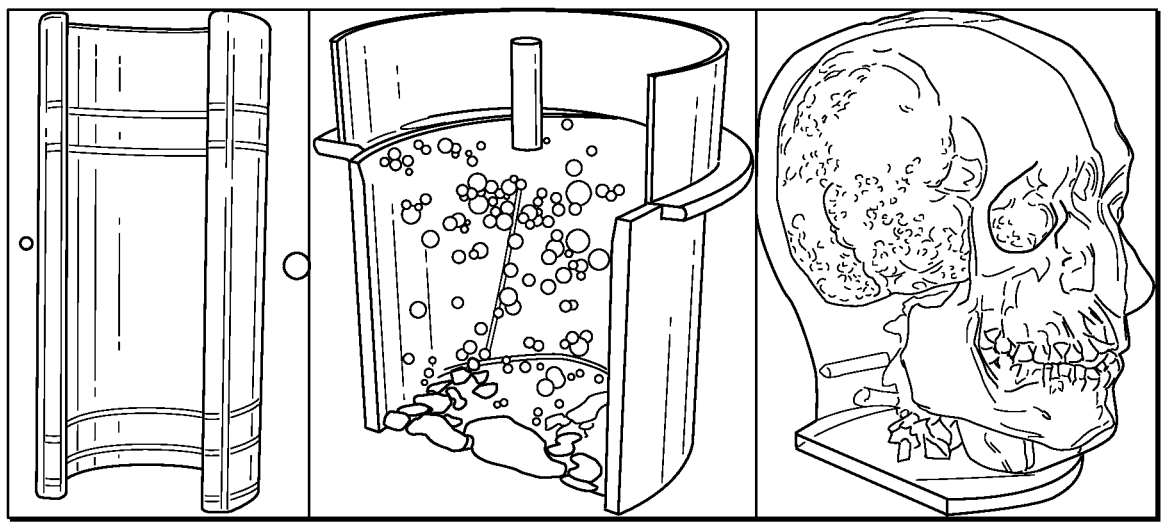

Three phantoms were used in this study: a cylinder phantom with a thin tungsten wire and several acrylic spheres; a clutter phantom in which acrylic and Teflon spheres were suspended in gelatin along with a tungsten wire; and an anthropomorphic head phantom also containing a tungsten wire insert. Each phantom was imaged twice in sequence, with each phantom shifted by several centimeters and tilted several degrees for the second acquisition to simulate (rigid) change in patient position from pre-op to intra-op setup. A CBCT bench was used, with each acquisition involving 360 projections obtained over 360° [1536×1536 pixels] at 100 kVp, 63 mAs. All images were reconstructed using 3D filtered backprojection with isotropic (0.5×0.5×0.5) mm³ voxels. FIGS. 7A and 7B illustrate image views of the phantoms for the experimentation.

Projections from the first acquisition were reconstructed using a standard geometric calibration procedure. Projections from the second acquisition were then registered to this 3D volume using the 3D-2D registration algorithm described above to obtain one PM per projection. A modified FDK algorithm was used for image reconstruction of the second set of images where the backprojection geometry for each projection was defined using the set of PMs.

To compare the results of the self-calibration to the reference calibration, image quality was examined between reconstructions through FWHM measurements of the point-spread function (PSF) created by the tungsten wire inserts for 10 axial slices. In addition, displacement of the perpendicular ray that connects the source to the piercing point was measured and compared by calculating the shortest distance from the ray to the point (0,0,0) within the object coordinate frame. The view-by-view magnification of the system was also compared between the "true" calibration and self-calibration methods.

The perpendicular ray placement associated with the two calibration methods corresponded closely for all projections (as shown in FIG. 8A). All of the displacements were less than 1 mm (at the detector), indicating that the self-calibration is placing the rays with sufficient precision to fall within the same 0.5 mm isotropic voxel of the reconstructed 3D image through backprojection. FIG. 8B shows the reference and calculated magnifications of the system for all projections. The sinusoidal nature of the magnification is due to slightly off-center positioning of the phantoms and differs by at most 3.2% between self-calibrated geometry and reference geometry. FIGS. 8A and 8B illustrate graphical views of the difference in perpendicular ray placement between true geometry and geometry found using 3D-2D registration and magnification of the system for each projection respectively.

Figure 9:
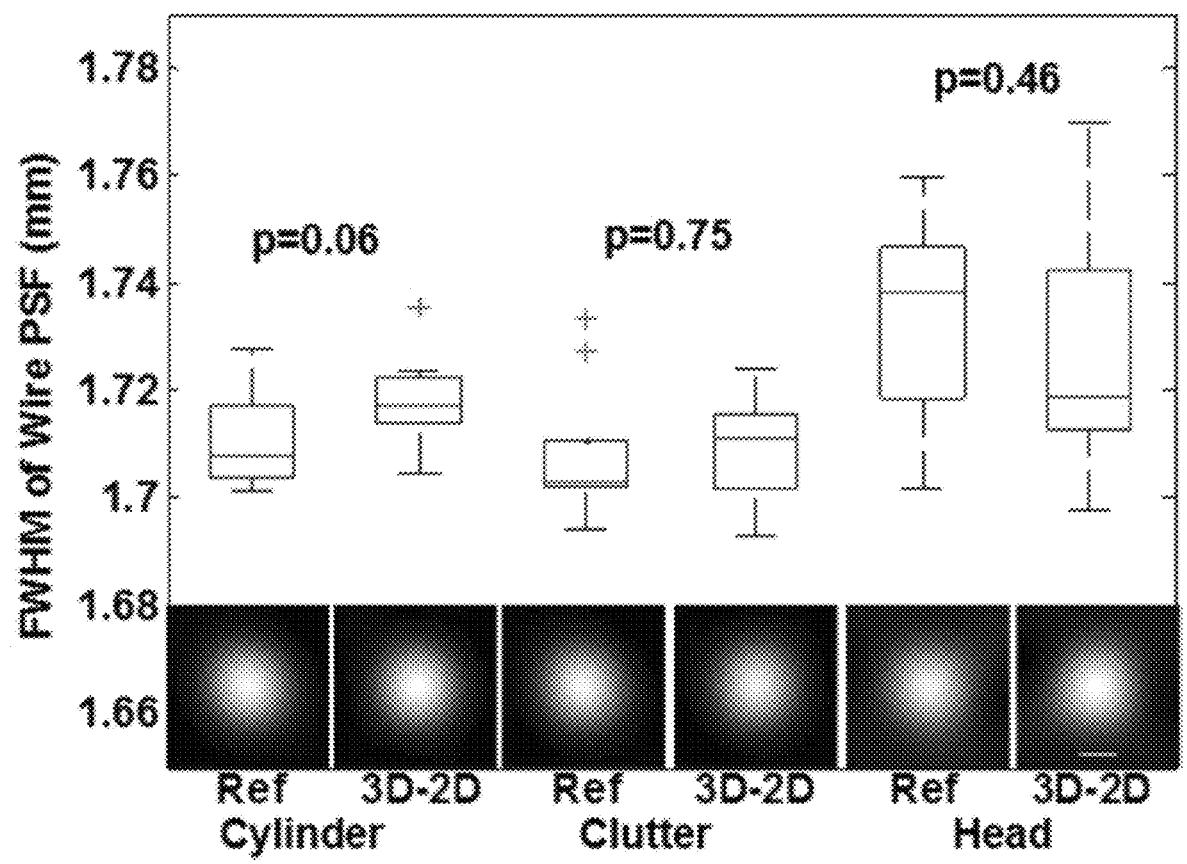
FIG. 9 illustrates a graphical view of boxplots of FWHM measurements of the wire PSF in each phantom. P values for the cylinder, clutter, and head phantom data sets are 0.06, 0.75, and 0.46 respectively.

None of the phantoms exhibited a significant difference in FWHM between the two calibration methods (p=0.06 for the cylinder phantom, p=0.75 for the clutter phantom, and p=0.46 for the head phantom) as shown in FIG. 9, indicating that the self-calibration method accurately corrected the perturbations imparted to the system geometry and yielded an image comparable to a standard calibration. FIG. 9 illustrates a graphical view of boxplots of FWHM measurements of the wire PSF in each phantom. P values for the cylinder, clutter, and head phantom data sets are 0.06, 0.75, and 0.46 respectively. Images of the PSF are shown with length bar marking 1 mm length in the far right image.

Figures 10A, 10B, 10C:
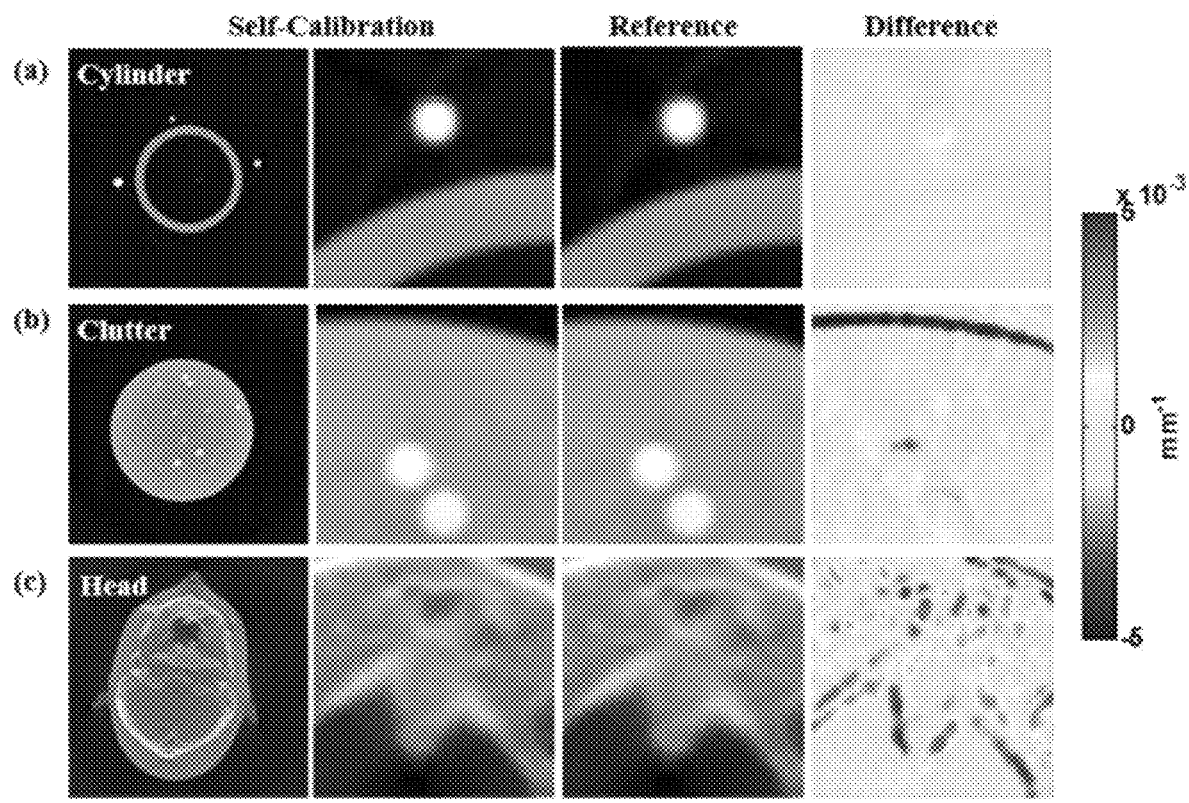
FIGS. 10A-10C illustrate 3D image reconstructions.

Visual inspection of the reconstructed 3D images in FIGS. 10A-10C shows that structures of interest are accurately reconstructed using the self-calibration at a level of image quality comparable to (and perhaps superior to) the reference calibration. Additionally, the residuals between the two images are on the order of $10^{-3}$ mm$^{-1}$ further showing that self-calibration computed an accurate representation of the system geometry despite poor initialization. FIGS. 10A-10C illustrate 3D image reconstructions. For each phantom in FIGS. 10A-10C reconstructed images using self-calibration shown in the first column, zoom on reconstructed image using self-calibration shown in the second column, zoom of same are from reconstruction using reference calibration shown in third column, difference between zoomed areas, shown in fourth column.

Figure 12:
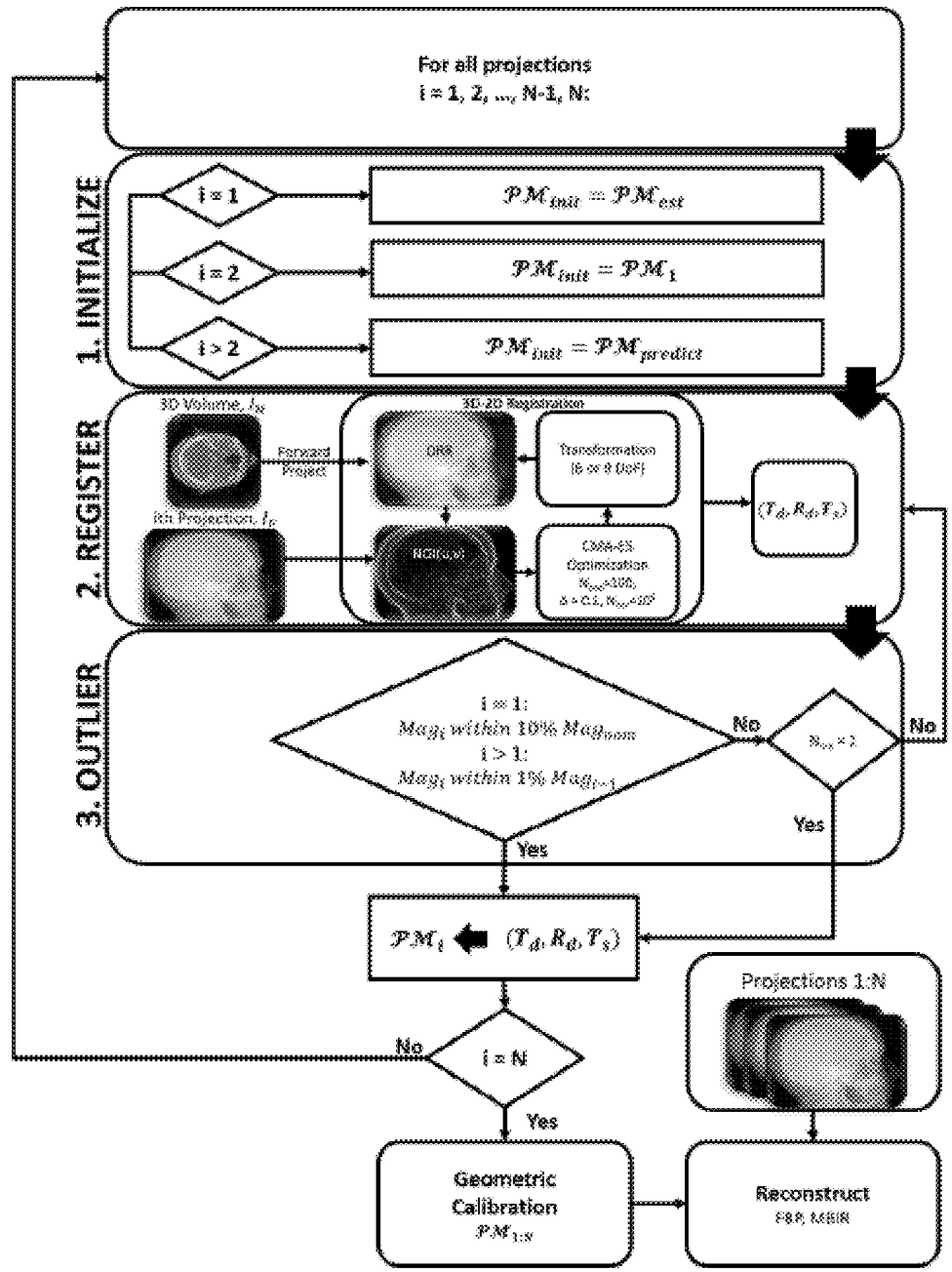
FIG. 12 illustrates a flowchart for the self-calibration process.

In another embodiment, the method for enabling volumetric image reconstruction from unknown projection geometry of tomographic imaging systems includes self-calibration. In image-guided interventions (IGI), a high quality CT image of the patient is commonly acquired prior to the procedure for diagnostic or planning purposes. Furthermore, during IGI, a series of CBCT images may be acquired—one at the beginning of the case, followed by CBCT acquisitions at particular milestones during, or at the conclusion of, the procedure. In these scenarios, the patient-specific 3D image can be registered to the 2D projection data acquired in subsequent CBCT acquisitions. Similar scenarios have been described for prior-image-based 3D image reconstruction to improve image quality and/or reduce radiation dose. For 3D-2D registration, a projection matrix ($\mathcal{PM}$) characterizing the system geometry is required for the forward projection of the 3D volume to create a 2D digitally reconstructed radiograph (DRR) to be registered to a 2D projection. The $\mathcal{PM}$ can be decomposed in terms of the 9 DoF describing the source position ($T_s$) and detector position ($T_d$) and rotation ($R_d$), where $T_s = [T_{s,x}, T_{s,y}, T_{s,z}]^T$, $T_d = [T_{d,x}, T_{d,y}, T_{d,z}]^T$ and $R_d = [R_{d,x}, R_{d,y}, R_{d,z}]^T$ as shown in FIG. 2. A simplifying assumption is that the source position, $T_s$, is fixed with respect to the detector, reducing the system geometry to 6 DoF. It is possible to determine the system geometry for each projection by solving for these 6 or 9 DoF using 3D-2D registration, and repeating the registration for all projections yields a geometric calibration of the system that can be used for 3D image reconstruction. FIG. 12 provides a flowchart for the self-calibration method: for each projection, the registration is initialized, registered via 3D-2D registration, and checked for outliers. Once a system geometry is found for all projections, a 3D volume is reconstructed—for example, by filtered backprojection (FBP) for simple circular orbits or by model-based image reconstruction (MBIR) for non-circular trajectories. FIG. 12 illustrates a flowchart for the self-calibration process. The system geometry for each 2D projection in a CBCT acquisition is determined by registering each projection to a previously acquired 3D image using a robust 3D-2D registration algorithm. The $i^{th}$ registration is initialized by a simple predictor based on the $(i-1)^{th}$ registration. Outliers are detected in results that violate constraints on the smoothness of the orbit or other known characteristics of system geometry (e.g., abrupt change or spurious values of magnification). Registration of all projection views provides the geometric calibration required for 3D image reconstruction.

Figure 11:
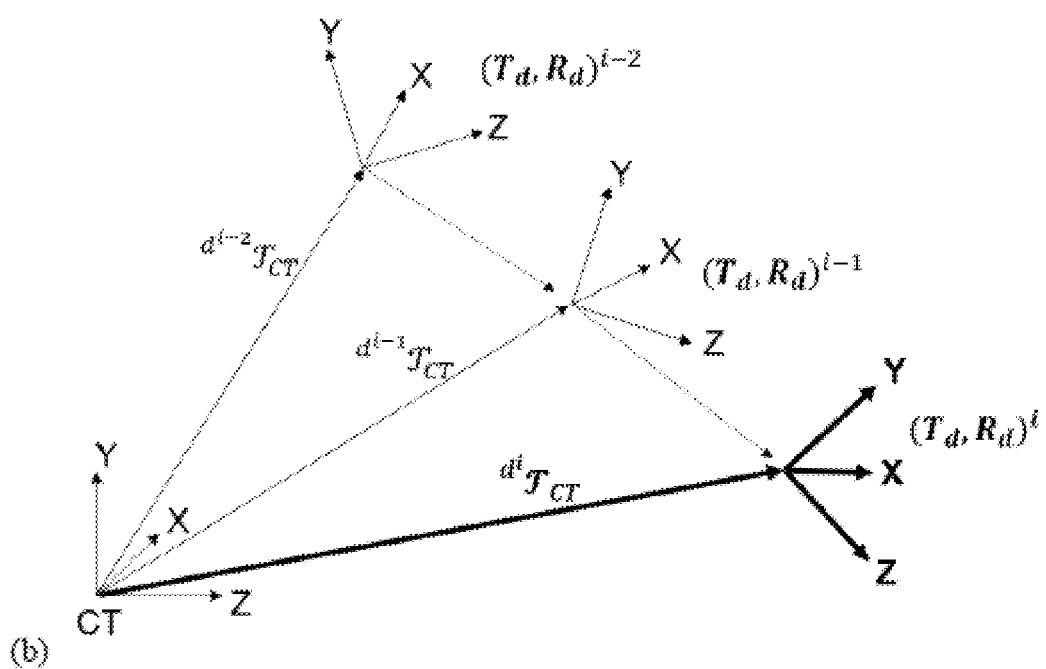
FIG. 11 illustrates a graphical view of an initialization of the $i^{th}$ registration for views i=3, . . . N) by linear extrapolation of the previous (i−1) and (i−2) registrations.

A $\mathcal{PM}$ is required to initialize the registration of each projection, $\mathcal{PM}_{init}$. For initialization of the first (i=1) projection, a coarse estimation of the projection matrix is used based on nominal parameters of the system geometry. Specifically, $T_d$ and $T_{s,z}$ are initialized according to the object-detector distance and detector-source distance, respectively. The orientation of the i=1 projection with respect to the patient (e.g., PA, AP, LLAT, or RLAT) could be simply obtained from information available in the DICOM data on patient and image orientation. As a brute force check on the initial i=1 orientation, the initial rotational values in $R_d$ are changed by increments of 90° about the 3 cardinal axes to account for all possible orientations, registered each of the 24 permutations (called $\mathcal{PM}_{est}$ in FIG. 12) and selected whichever yielded maximum similarity as $\mathcal{PM}_1$. The second (i=2) view was initialized simply using $\mathcal{PM}_1$ from registration of the first projection. For projections i=3, . . . , N, the registration is initialized as illustrated in FIG. 11 using a predicted projection matrix, $\mathcal{PM}_{predict}$, computed using the geometries of the previous two views. FIG. 11 illustrates a graphical view of an initialization of the $i^{th}$ registration for views i=3, . . . N) by linear extrapolation of the previous (i−1) and (i−2) registrations.

To initialize views i=3, . . . , N, as illustrated in FIG. 11, a prediction estimates the position of the detector as it moves around the object and is used to compose $\mathcal{PM}_{predict}$. This prediction is a linear extrapolation in the 6 DoF describing detector position and rotation, $(T_{d,d})$. The three DoF describing the source position ($T_s$) are not extrapolated as it is not expected that the source should move significantly with respect to the detector. The prediction is formed based on the geometries of the previous two views by solving the transformation from $(T_d, R_d)$ i−2 to $(T_d, R_d)$ i−1, where i is the current view:

$$^{d^{i-1}}T_{d^{i-2}} = {^{d^{i-1}}T_{CT}} \cdot ({^{d^{i-2}}T_{CT}})^{-1}.$$

The transform $^{di}T_{d\ i=2}$ indicates the homogeneous transformation from 3D CT coordinates to 3D detector coordinates for the $i^{th}$ view, and the transform $^{di-1}T_{d\ i=2}$ indicates the homogeneous transformation from 3D detector coordinates for the $(i-2)^{th}$ view to the $(i-1)$ view. This transformation is then applied to $(T_d, R_d)^i$ to obtain a prediction for $(T_d, R_d)^i$:

$$^{d^i}T_{CT} = {^{d^{i-1}}T_{d^{i-1}}} ({^{d^{i-1}}T_{CT}}),$$

which is then taken as initialization for registering the $i^{th}$ view.

The 3D-2D registration method central to the self-calibration method incorporates normalized gradient information (NGI) as a robust similarity metric within the covariance matrix adaptation-evolution strategy (CMA-ES) optimizer. A linear forward projector implemented on GPU computes the DRR for a particular system pose. Similarity (NGI) is computed between the CT (by way of its DRR, taken as the moving image, IM) and the 2D projection (taken as the fixed image, IF) as:

$$NGI(I_F, I_M) = \frac{GI(I_M, I_F)}{GI(I_F, I_F)},$$

$$GI(p_1, p_2) = \Sigma_{i,j \in \Omega} m(i,j) w(i,j) \min(|\nabla p_1(i,j)|, |\nabla p_2(i,j)|),$$

$$\nabla p(i,j) \triangleq \left(\frac{d}{di} p(i,j), \frac{d}{dj} p(i,j)\right),$$

$$w(i,j) = \frac{1}{2}\left(\frac{\nabla p_1(i,j) \cdot \nabla p_2(i,j)}{|\nabla p_1(i,j)| \cdot |\nabla p_2(i,j)|} + 1\right).$$

NGI exhibits robustness against content mismatch arising from non-rigid anatomical deformation or the presence of surgical tools introduced in the radiograph. The CMA-ES optimizer was used to solve for the transformation that maximizes NGI:

$$\tilde{T_s}, \tilde{T_d}, \tilde{R_d} = \underset{T_s, T_d, R_d \in S}{\operatorname{argmax}} NGI(I_M, I_F(T_s, T_d, R_d)).$$

Parameter selection in the CMA-ES optimization included downsampling of both the DRR and the projection image by a factor of 3 and population size ($N_{pop}$) set to 100. The stopping criterion was set to changes ($\Delta$) in translation or rotation of less than 0.1 mm or 0.1° respectively, or a maximum of 106 iterations ($N_{max}$). From the resulting geometry estimate of the source and detector, a $\mathcal{PM}$ is formed as:

$$\mathcal{PM} := \begin{pmatrix} T_{s,z} & 0 & T_{s,x} & 0 \\ 0 & T_{s,z} & T_{s,y} & 0 \\ 0 & 0 & 1 & 0 \end{pmatrix} \begin{pmatrix} \mathcal{R}_{3\times3}(R_{d,x}, R_{d,y}, R_{d,z}) & \begin{matrix} T_{d,x} \\ T_{d,y} \\ T_{d,z} \end{matrix} \\ 0\ 0\ 0 & 1 \end{pmatrix}.$$

where $\mathcal{R}_{3\times3}$ represents a 3D rotation matrix with center of rotation at the origin of the CT volume coordinate system. With respect to order of operations, the rotational operations are applied before translations. The present self-calibration method generates a $\mathcal{PM}$ for all projections acquired in a CBCT scan.

It is possible to identify outliers in pose estimation by detecting spurious values of the system parameters (or combinations of system parameters) resulting from image registration. System magnification [the ratio of $T_{s,z}$ and $(T_{s,z}-T_{d,z})$] was selected as a simple metric for outlier detection, because the ratio allows fluctuations in scale that do not affect the forward- or back-projection of rays in 3D image reconstruction, but traps errors that would distort the projection matrix. Each registration result is checked as a possible outlier. For the i=1 projection, the resulting magnification must be within 10% of that calculated from the known, nominal system magnification (Magnom, computed from the source-object distance ($T_s$-$T_{d,z}$) and source-detector distance ($T_{s,z}$) provided for initialization of the first view). If the magnification is not within this range, then the algorithm must be reinitialized. For the i=2 projection, the magnification must be within 1% of the magnification associated with the i=1 projection for the algorithm to continue. If the magnification does not fall within this range, then registration for the i=2 projection is restarted using the same initialization method as the i=1 projection as detailed above. For all subsequent (i≥3) projections, the magnification must be within 1% of the magnification associated with the previous projection, and for any view implying magnification outside of this range, the registration is restarted using $\mathcal{PM}_{i-1}$ to initialize (instead of $\mathcal{PM}_{predict}$). If the resulting magnification is again not within the 1% error range, then the registration is restarted with the same initialization method as the i=1 projection. After this second repetition of the registration ($N_{rep}=2$), the result is accepted as the correct geometry, and the self-calibration algorithm continues to the next projection. (In the current study, as detailed below, there were few, if any, outliers for the fairly smooth orbits considered.) If the registration result is not an outlier, the geometry estimate is used to compose $\mathcal{PM}_i$. The outlier detection method was tested by running the self-calibration algorithm on CBCT data acquired in a circular orbit with 360 projections and a magnification of 1.5 using the experimental bench described below. The predicted pose for each view was purposely perturbed with Gaussian noise with σ=20 mm and 20° to stress the registration.

The proposed methodology was tested using the CBCT imaging bench and clinical robotic C-arm (Artis Zeego, Siemens Healthcare) shown in FIGS. 1A and 1B respectively. The bench includes an x-ray tube (RAD13, Dunlee, Aurora Ill.), flat-panel detector (PaxScan 4030CB, Varian, Palo Alto Calif.), and computer controlled motion system (Compumotor 6k8, Parker Hannifin, Rohnert Park Calif.) for acquisition of CBCT data in a variety of system configurations. For all studies involving the experimental bench, $T_d$, and $T_{s,z}$ were fixed to the nominal values of the Zeego C-arm (40 and 120 cm, respectively). The nominal scan technique involved 360 projections over 360° at 70 kVp and 227 mAs. For the Zeego system, $T_d$, and $T_{s,z}$ were nominally fixed to 40 and 120 cm respectively, and acquisitions obtained 496 projections over 200° at 87.2 kVp and 229 mAs. The nominal geometric calibration for the bench system was formed using a cylindrical phantom containing a pattern of steel BBs from which the full 9 DoF geometry of the source and detector can be determined for each projection in a CBCT scan. Alternatively, the nominal calibration for the Zeego C-arm was obtained using a clinical calibration tool—a cylindrical phantom with a spiral BB pattern. In each case, the nominal geometric calibration is referred to below as the "Reference Calibration."

Figure 13A:
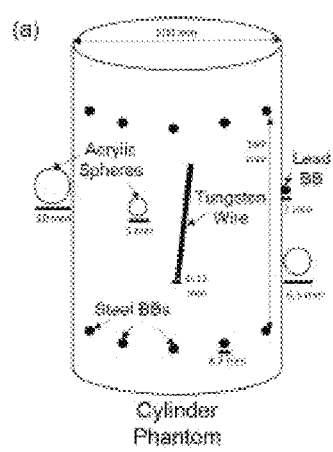
FIG. 13A illustrates a cylindrical phantom that combines the reference calibration of Cho (two circular patterns of steel BBs) with a tungsten wire, lead BB, and acrylic spheres to test geometric accuracy of the CBCT reconstruction.
Figure 13B:
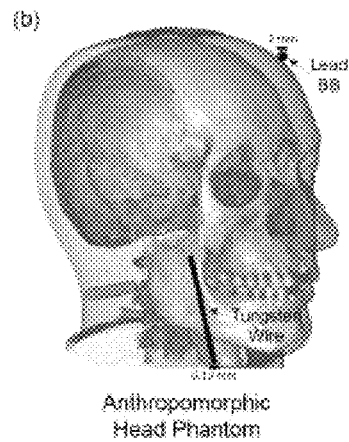
FIG. 13B illustrates an anthropomorphic head phantom with a tungsten wire and lead BB.

CBCT images from the bench and Zeego systems were reconstructed by FBP for cases of a nominally circular orbit (Experiments 1, 2, and 3, below). A model-based image reconstruction (MBIR) method was used to reconstruct images for the case of a non-circular orbit considered in Experiment 4 (below). The MBIR utilized a forward model that accounted for a generalized (non-circular) orbit to solve for the reconstructed image by maximizing the consistency of the image with the projection data, while also accounting for the statistics of the measured data. A penalized-likelihood (PL) objective function was used for this maximization, and the reconstructed image was computed in 50 iterations of 20 subsets with regularization strength $\beta=10^2$. Two imaging phantoms were used to evaluate the performance of the "Self-Calibration" in comparison to the "Reference Calibration". The first illustrated in FIG. 13A used the same cylindrical phantom as used in the Cho calibration (above) with the addition of a 0.13 mm diameter tungsten wire suspended along the central axis and a 2 mm diameter lead BB and 3 acrylic spheres (5, 6.5, and 10 mm diameter) attached to the surface of the cylinder. This configuration provided data in which the geometric calibration data (derived from the steel BBs) and the data for imaging performance assessment (derived from the tungsten wire, lead BB, and acrylic spheres) were identical, eliminating the question of orbit reproducibility. A second phantom, illustrated in FIG. 13B, involved a natural human skull in tissue-equivalent plastic with the addition of a 0.13 mm diameter tungsten wire inserted in the oropharynx and a 2 mm diameter lead BB attached to the surface. FIGS. 13A and 13B illustrate side views of imaging phantoms. FIG. 13A illustrates a cylindrical phantom that combines the reference calibration of Cho (two circular patterns of steel BBs) with a tungsten wire, lead BB, and acrylic spheres to test geometric accuracy of the CBCT reconstruction. FIG. 13B illustrates an anthropomorphic head phantom with a tungsten wire and lead BB.

Four experiments were conducted to test the performance of the self-calibration method, progressing systematically from simple geometries and objects (e.g., the bench and cylinder phantom) to more complicated scenarios (the Zeego and head phantom). In each case, the reference calibration was acquired using the Cho or spiral BB phantom as described above. The 3D image input to the self-calibration method was a distinct scan in each case (i.e., not the same as the projection data acquired in the current CBCT scan)—formed either from a previous CBCT scan or a previous CT scan on a diagnostic CT scanner. In each case, the calculated system geometry and CBCT images reconstructed using the self-calibration method (for both 6 and 9 DoF characterization of the system geometry) were compared to those from the reference calibration.

Experiment 1:

Cylinder phantom on imaging bench. Experiment 1 involved the cylinder phantom imaged on the CBCT bench to test the feasibility of the self-calibration method and obtain quantitative analysis of basic performance. A circular orbit was used, with the nominal scan technique described above. A previous CBCT scan of the phantom formed the 3D image input to the self-calibration method, with the previous scan acquired with an angular offset in projection views so that the projections used in 3D reconstruction were not identical to those in 3D-2D registration.

Experiment 2:

Anthropomorphic head phantom on imaging bench. Experiment 2 involved the anthropomorphic head phantom imaged on the CBCT bench to test the robustness of 3D-2D registration under more clinically/anatomically realistic conditions of x-ray scatter, image noise, and complexity of the subject. A previous scan of the head phantom on a diagnostic CT scanner (Siemens Somatom Definition, 120 kVp, 227 mAs, (0.46×0.46×0.40 mm$^3$) voxels) formed the 3D image input to the self-calibration method.

Experiment 3:

Anthropomorphic head phantom on robotic C-arm. Experiment 3 involved the anthropomorphic head phantom imaged on the Artis Zeego to test the method in a clinically realistic system geometry and orbit. A previous CBCT scan of the head phantom acquired using the Zeego formed the 3D image input to the self-calibration method. To challenge the method further, a realistic, pronounced change in image content was produced between the previous 3D image and the projection images acquired in the current CBCT scan— viz., a 2 mm diameter steel biopsy needle placed in the nasal sinuses and positioning the head with a strong) (~30° canthomeatal tilt to mimic a typical clinical setup. The reference calibration (using the spiral BB phantom mentioned above) was performed by the system service engineer as part of regular preventative maintenance within 6 months of the current scan in accordance with standard clinical practice.

Experiment 4:

Non-circular orbit. Experiment 4 tested the self-calibration algorithm on a non-circular orbit—specifically, a saddle-shaped orbit that could be used to extend the longitudinal field of view, reduce cone-beam artifacts, or improve image quality in the manner of task-driven imaging—all cases for which a conventional geometric calibration acquired prior to the scan may be irreproducible or infeasible. The scan was conducted on the CBCT bench using the anthropomorphic head phantom with the same nominal scan protocol as above, except that the source and detector were moved along the Y and Z axes (as defined in FIG. 11 and shown in FIGS. 1A and 1B) during the scan to produce the saddle trajectory illustrated in FIGS. 14A and 14B. The total deviation in both $T_d$ and $T_{s,y}$ was ±25 mm to maintain approximately the same field of view as previous experiments within the constraints of the test bench system. As in Experiment 2, a previous diagnostic CT scan of the head provided the 3D image input to the self-calibration method. A CBCT image was reconstructed using the MBIR method described above and the self-calibration result for system geometry. Since the reference calibration method strictly holds only for circular orbits, an image of the head phantom scanned in a circular orbit was used as a reference and basis of image quality comparison (using the same MBIR method for reconstruction). FIGS. 14A and 14B are graphical views of the saddle orbit for Experiment 4. FIG. 14A shows a polar plot showing magnification for the saddle and circular orbits. FIG. 14B illustrates $T_d$, and $T_{s,yz}$ for the saddle and circular orbits.

Performance was evaluated in terms of three measures of image quality/geometric accuracy of the self-calibration method in comparison to conventional reference calibration. The first was the full-width at half-maximum (FWHM) of a point spread function (PSF) measured from the tungsten wire in each phantom. From CBCT images reconstructed with (0.05×0.05×0.05) mm$^3$ isotropic voxels, line profiles through the center of the wire in 10 axial images were sampled radially over 360°. A Gaussian distribution was fit to each line profile, and the FWHM was averaged over all line profiles and slices. The second performance measure was the reprojection error (RPE) associated with the position of (the centroid of) the lead BB placed on the surface of both phantoms. The BB centroid was localized in each 2D projection of the scan data using a Gaussian fit about the BB position. The centroid position was then transformed into 3D space using the $\mathcal{PM}_i$ corresponding to each projection, and its location on the detector was connected to the calibrated 3D source location by a line segment. This process was repeated for all projections, and the closest point of intersection for line segments spaced 90° apart was computed, yielding a point cloud. The width of this point cloud was evaluated using principal component analysis (PCA) and averaging the lengths of the principal components.

$$RPE = \frac{1}{K}\Sigma_{k=1}^{K}|V_k|,$$

where $V_k$ is a principal component of the 3D data and $K \leq 3$. Analysis in terms of PCA is analogous to simply evaluating the width of the point cloud (e.g., by Gaussian fit) but better accommodates possible bias in the orientation of the point cloud. Finally, the performance of geometric calibration was assessed with respect to the quality of 3D image reconstructions themselves. Each was qualitatively evaluated in terms of blur, noise, and artifacts associated with geometric calibration errors—e.g., streak artifacts and distortion of high contrast details such as the temporal bone trabeculae.

Figure 15:
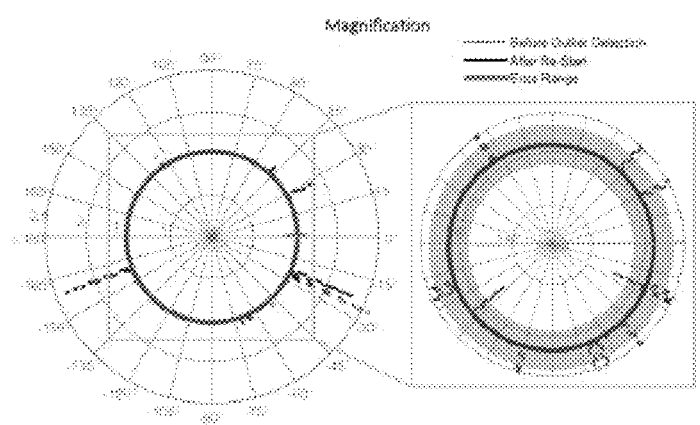
FIG. 15 illustrates a graphical view of outlier detection.

In all of the experiments reported below, there were no outliers detected in the self-calibration data, indicating a suitable degree of robustness of the 3D-2D registration process. This includes the various forms of initialization for the i=1 and i=2 projections, the prediction method for initializing the i≥3 projections, the similarity metric (NGI) even in the presence of image content mismatch (e.g., the biopsy needle in Experiment 3), and the CMA-ES optimization method. To stress test the outlier detection and recovery method, a study was conducted as described above in which the geometry estimates were purposely perturbed. Example results are shown in FIG. 15, where the magnification is plotted as a function of projection view angle before outlier detection (dashed black line) and after detection and recovery (solid black line). Following perturbation, 12 outliers were detected among the 360 projections, and all were recovered by the re-start method described above (re-starting and/or using the previous view for initialization). FIG. 15 illustrates a graphical view of outlier detection. The dashed black line shows the magnification of the registration before outlier detection using a perturbed initialization ($\alpha$=20 mm, 20°). The solid black line shows the magnification after outlier detection and re-starting the registration using the previous view for initialization. The grey region represents the window for allowable magnification (10% for the i=1 view, 1% for subsequent views).

Figures 16A, 16B, 16C, 16D, 16E, 16F, 16G, 16H, 16I, 16J, 16K, 16L:
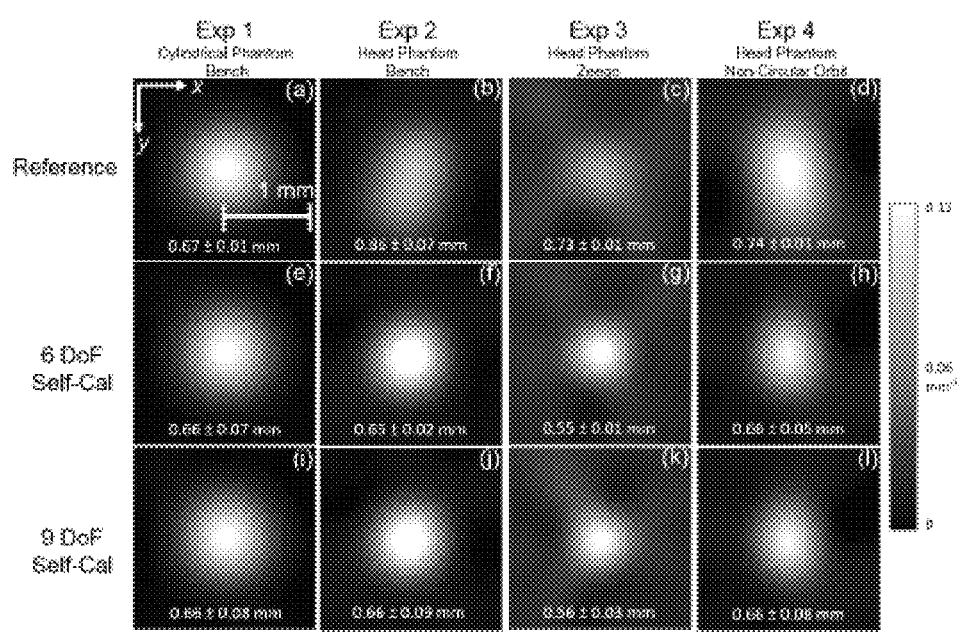
FIGS. 16A-16L illustrate image views of the effect of geometric calibration on spatial resolution (FWHM of the PSF).

The PSF about the tungsten wire in Experiments 1-4 is shown in FIGS. 16A-16L for the reference calibration (top row) and the self-calibration using both 6 DoF (middle row) and 9 DoF (bottom row) representation of system geometry. Overall improvement is seen for self-calibration compared to reference calibration—both quantitatively (FWHM for each case) and qualitatively (apparent distortion and intensity of the PSF). For Experiment 1 (cylinder phantom on the imaging bench; FIGS. 16A, 16E, and 16I), the PSFs are comparable, indicating that self-calibration performs as well as (simultaneous) reference calibration for a simple object on a near-perfect system (stable, high-precision imaging bench).

Experiment 2 (head phantom on the imaging bench; FIGS. 16B, 16F, 16J) shows improvement in FWHM (0.66 mm for self-calibration, 0.86 mm for reference calibration, p<0.001) as well as the general shape and intensity of the PSF. Note that the wire in the head phantom was located ~9 cm inferior to the central axial slice (whereas the wire in the cylinder phantom of Experiment 1 was analyzed at the central axial slice). The improvement compared to the reference calibration likely indicates that while the reference calibration is suitable near the central slice (FIG. 16A) it may include errors in detector angulation that become apparent farther from isocenter (FIG. 16B). An alternative explanation is that the scan geometry was slightly irreproducible between the reference calibration and the current scan (whereas Experiment 1 involved simultaneous imaging and calibration in the same phantom); however, this is less likely, since the imaging bench is rated to a fairly high degree of reproducibility (~0.001 mm) in positioning of the motion control system. Also, previous work showed that detector angulation is among the more difficult parameters to estimate in reference calibration and can have a large impact on the geometric accuracy of CBCT reconstructions.

Experiment 3 (head phantom on the Zeego; FIGS. 16C, 16G, and 16K) shows measurable improvement of the PSF using self-calibration compared to the standard clinical reference calibration. The two most likely explanations are similar to those noted above: (1) slight intrinsic errors in the reference calibration; and/or (2) slight differences between the reference calibration and current scan, owing either to irreproducibility of the C-arm orbit and/or aging of the reference calibration over time. Finally, FIGS. 16D, 16H, and 16L show the results of Experiment 4 involving the head phantom on the imaging bench with a non-circular orbit. Note that the reference for comparison (FIG. 16D) is for a circular orbit (calibrated with the Cho phantom), and all images were reconstructed with MBIR using the same regularization and optimization parameters. The results demonstrate the feasibility of self-calibration for non-circular orbits, suggesting the same level of geometric accuracy in pose estimation as for circular orbits (Experiments 1 and 2) and compatibility of the resulting geometry estimates with MBIR. Comparing the self-calibration results for 6 DoF (FIG. 16E-16H) and 9 DoF (FIG. 16I-16L characterization of system geometry, no appreciable (or statistically significant) differences in the PSF or FWHM are seen, implying relative insensitivity to the additional 3 DoF associated with variations in source position relative to detector for the systems considered in this work. This is not a surprising result for the imaging bench (for which the source is rigidly fixed with respect to the detector) and suggests that possible variations in source position on the Zeego (e.g., due to C-arm flex under gravity) are minor with respect to the PSF of image reconstructions.

FIGS. 16A-16L illustrate image views of the effect of geometric calibration on spatial resolution (FWHM of the PSF). Images show an axial slice through the tungsten wire in the cylinder or head phantom. FIGS. 16A-16D show images reconstructed using the reference calibration. FIGS. 16E-16H show images reconstructed using self-calibration and 6 DoF characterization of system geometry. FIGS. 16I-16L show images reconstructed using self-calibration and 9 DoF characterization of system geometry. Each column represents one of the four experiments detailed in Methods.

FIGS. 17A and 17B illustrate graphical views that summarize the results for the four experiments in terms of the RPE, echoing the results of FIGS. 16A-16L. FIG. 17A shows an example point cloud from which the RPE was determined as detailed above, and FIG. 17B shows the improvement in RPE obtained by self-calibration in comparison to reference calibration. For Experiment 1, a statistically significant improvement in RPE (~0.69 mm for self-calibration) is shown compared to reference calibration (0.83 mm) under ideal conditions (p<0.001). This also shows RPE to be a more sensitive test of geometric calibration than PSF width (FIGS. 16A, 16E, and 16I). Experiment 2 demonstrates an additional characteristic of self-calibration: the 6 DoF self-calibration was significantly improved compared to reference calibration (RPE=0.61 mm versus 0.84 mm, p<0.001); in addition, the 6 DoF self-calibration was superior to the 9 DoF self-calibration (RPE=0.61 mm versus 0.82 mm, p<0.001). This result may seem counterintuitive and points to an interesting characteristic of self-calibration: the 9 DoF method allows potentially unrealistic variations in source position with respect to the detector—e.g., excursions in Ts,z; while FBP reconstruction image quality (FIGS. 16F and 16J) may be relatively insensitive to such excursions since backprojected rays are still along the correct lines (recognizing a fairly small effect associated with distance weighting), the difference is evident in the RPE among orthogonal rays. The 6 DoF self-calibration holds the position of the source fixed with respect to the detector, which appears to incur less error in geometry estimation, at least for the rigid geometry of the imaging bench. For Experiment 3, the mean and median RPE are lower for the self-calibration methods than the reference calibration method, but the difference was not statistically significant (p=0.08). The overall performance appears better (consistent with FIGS. 16C, 16G, and 16K), but errors in finding the BB centroid in the projection images may have contributed to a reduction in reliability of the RPE estimates. Another factor is that the C-arm undergoes significant deviations from a circular orbit, which broadens the point cloud distributions. Experiment 4 is not shown, since RPE assumes a circular orbit.

FIGS. 17A and 17B illustrate graphical views of an effect of geometric calibration on RPE. FIG. 17A illustrates an examplary point cloud distribution used to measure the RPE, generated by backprojecting the centroid of a BB in each projection and finding the closest point of intersection between orthogonal views. FIG. 17B illustrates the RPE resulting from 6 and 9 DoF self-calibration compared to conventional reference calibration. An asterisk indicates significant difference from the reference, an open circle indicates mean value, a horizontal line indicates median value, a closed box indicates interquartile range, and whiskers indicate full range of the data.

FIGS. 18A-18J illustrate the effects quantified above in terms of qualitative visualization of high-contrast details in the anthropomorphic head phantom, including streaks (from a high-contrast biopsy needle) and distortion (wisps about cortical bone and temporal bone trabeculae). Images from Experiment 1 are not shown, because they were essentially identical: both reference calibration and self-calibration yielded qualitatively accurate reconstruction of the cylinder phantom without appreciable geometric artifacts. The same result is seen for Experiment 2 (FIGS. 18A, 18D, and 18G), where both reference and self-calibration yield a qualitatively accurate reconstruction of the skull. Other sources of image quality degradation include x-ray scatter, beam hardening, etc., but not geometric calibration. Experiment 3 demonstrates noticeable improvement in images reconstructed using self-calibration, evident as a reduction in streak artifact arising from the high-contrast biopsy needle located at the anterior aspect of the axial slice in FIGS. 18B, 18E, and 18H. The reduction in streaks indicates that the artifacts are not solely attributable to metal artifact, but are in part also a result of an imprecision in geometric calibration that is accentuated in the reconstruction of a high-contrast, high-frequency objects such as a needle. The self-calibration method yields a more accurate geometric calibration and is more robust against such streak artifacts.

Figures 18A, 18B, 18C, 18D, 18E, 18F, 18G, 18H, 18I, 18J:
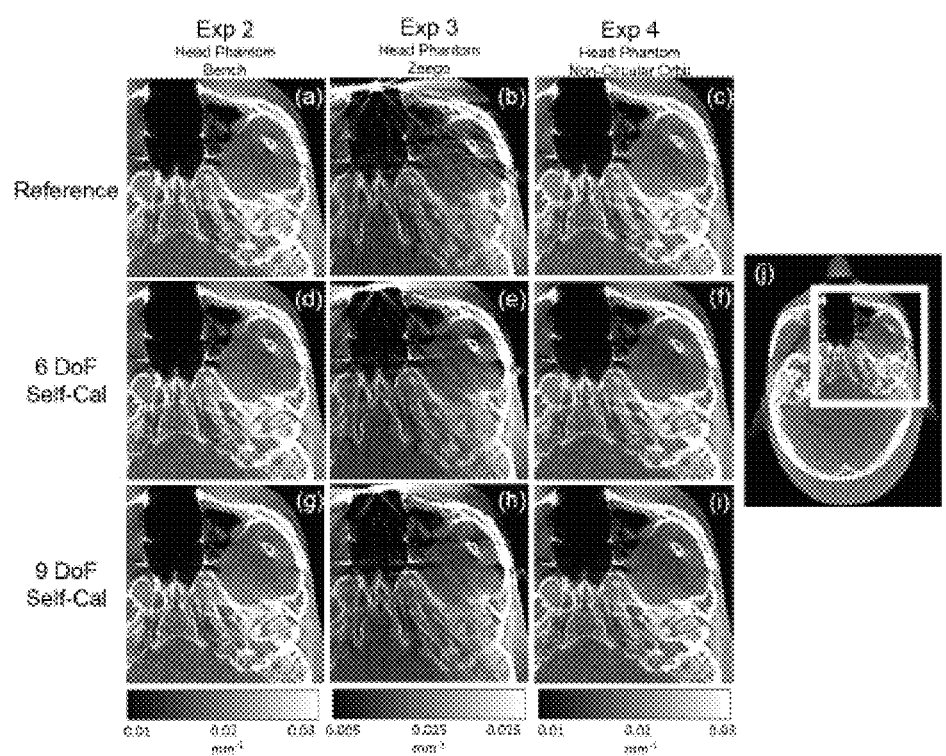
FIGS. 18A-18J illustrate image views of the effect of geometric calibration on image quality.

Experiment 4 shows MBIR images formed using reference and self-calibration methods, the former for a circular orbit and the latter for a saddle orbit. The results are qualitatively identical, with both methods yielding calibration suitable for MBIR. Minor differences in cone-beam artifacts may be appreciated in FIGS. 18F and 18I compared to FIG. 18C, but that is due to the non-circular orbit, not the fidelity of geometric calibration. Overall, even in cases for which the difference between reference calibration and self-calibration is negligible, the results are positive findings: they demonstrate not only the feasibility to compute a geometric calibration using the proposed method, but also that the resulting calibration is comparable to well-established methods for reference calibration; moreover, the self-calibration method is extensible to non-circular orbits and imaging systems for which reference calibration is irreproducible or infeasible.

FIGS. 18A-18J illustrate image views of the effect of geometric calibration on image quality. FIGS. 18A-18C illustrate a zoomed region of an axial slice of the head phantom in Experiments 2-4 reconstructed using reference calibration. FIGS. 18D-18F illustrate the same, reconstructed using the 6 DoF self-calibration and FIGS. 18G-18I illustrate the 9 DoF selfcalibration. FIG. 18J illustrates the full axial field of view and zoom region.

The self-calibration method presents a promising means to obtain accurate geometric calibration not only for standard circular orbits and presumably well calibrated systems, but also for more complicated non-circular orbits and/or systems for which system geometry is unknown/irreproducible. The study detailed above demonstrates that the self-calibration method yields system geometry sufficient to reconstruct images with comparable or improved image quality compared to reference calibration methods and is extensible to cases where conventional reference calibration may not be possible—e.g., non-circular orbits. It is interesting to note that while both 6 and 9 DoF self-calibration performed better overall than the reference calibrations, the 6 DoF self-calibration method slightly outperformed the 9 DoF self-calibration, specifically in Experiment 2. This may indicate that although the 9 DoF method yields a more complete system description, it may be subject to local minima in the larger search space. With the 6 DoF method, the 3 DoF describing the source position are held fixed and reduce the search space in a manner that appears to reduce susceptibility to such local minima and is consistent with the mechanical rigidity of the robotic C-arm used in this work. It is also possible that the 9 DoF optimization is more susceptible to image noise. The optimization was not strongly affected by propagation of error from previous views to the next, even though the algorithm is sequential in nature and uses previous views to initialize the next. In addition to trapping outliers as described in Section 2.5, the registration for each view is computed de novo (i.e., with a new CMA-ES population and a search for the current pose that is largely independent of the previous pose) and demonstrates capture range that is more than sufficient to recover from small errors in $\mathcal{PM}_{init}$ resulting from previous views. The primary objective of the current study was to assess the feasibility and geometric accuracy of the self-calibration method; accordingly, the run-time of the algorithm was not fully optimized. The algorithm was implemented in Matlab (The MathWorks, Inc, Natick Mass.) and yielded a run-time of approximately 3 seconds per registration for the 6 DoF method (or 5 seconds per registration for the 9 DoF method), excluding the projections for which multiple initializations are used and scale the registration time accordingly. A variety of ways to reduce the run-time for a complete scan could be developed in future work, such as parallelizing registrations by binning the projections into sub-groups and registering these groups in parallel (as opposed to registering all projections sequentially), or simultaneously registering more than one projection during the same optimization. Among the limitations of the algorithm is that the accuracy of registration is dependent on the quality of the 3D volume and the 2D images forming the basis of registration. However, as shown in Experiment 3 where a CBCT image acquired from the Zeego system was used as the 3D volume for registration, the registration algorithm is fairly robust to artifacts present in the 3D images (e.g., cone-beam artifacts, scatter, truncation, etc.). A second limitation is its dependence on the initialization of the geometric parameters in the first view, and poor initialization could result in registration failure. Initialization is most important for the first projection, which requires knowledge of the nominal system parameters, since if the first projection fails to register correctly, the algorithm may be unable to proceed. Another limitation is that the registration between the 3D volume and 2D projections is limited to affine transformations that presume rigid patient anatomy. Although limited to affine transformations, the registration is still fairly robust against anatomical deformation, as described in previous work, since the similarity metric incorporated in the registration process uses strong edges consistent in both images, which in CBCT most likely represent rigid, bony structures. Registration therefore aligns consistent bony structures in the images while tending to ignore soft tissue deformations. Such robustness to deformation was previously investigated in the context of spine surgery, where it was found that the 3D-2D registration framework was able to register images with a median projection distance error of 0.025 mm even under conditions of strong deformation (e.g., preoperative CT with the patient oriented supine and the spine straight (or lordotic) registered to an intraoperative projection image in which the patient is oriented prone with the spine in kyphosis). A multi-resolution pyramid and a multi-start optimization method could be incorporated in the self-calibration algorithm at the cost of computation time. This suggests the potential for application to imaging sites beyond purely rigid anatomical contexts such as the cranium, including the spine and pelvis, for example. Such application remains to be fully investigated, but initial results on robustness of the registration appear promising, particularly if the region of interest is small (e.g., a few vertebral levels), thereby better satisfying conditions of local rigidity that can be approximated by affine transformation. The current study did not specifically investigate the effect of patient motion, and while good patient immobilization is certainly good practice, it is worth noting that the self-calibration method described here can be extended to provide a means for correction of patient motion. Just as the 3D-2D registration of each view characterizes the source and detector pose with respect to the patient (i.e., to the CT image), (rigid) motion of the patient in each projection view is encoded into the projection matrices; therefore, patient motion is effectively seen as virtual motion of the C-arm and is therefore mitigated in the 3D image reconstruction. The patient motion must be affine (e.g., shift or tilts of the head position during the scan), and the method would not be expected to work well for deformable motion (e.g., respiratory motion of the diaphragm). In a similar manner as described above with respect to robustness to anatomical deformation, the method may be applicable to contexts involving a small region of interest within which the motion can be approximated as affine. Such application of the self-calibration algorithm to motion correction is the subject of ongoing future work. In summary, the self-calibration method performed as well as a reliable (up-to-date) reference calibration on a highly stable CBCT imaging bench and performed better than the reference calibration (subject to periodic quality assurance updates) on a clinical robotic C-arm. This indicates that self-calibration could improve 3D image reconstruction even for presumably well calibrated systems and could offer a sentinel alert against "aging" of the reference calibration. The algorithm demonstrated robustness to changes in the image between the 3D volume and the 2D projection data, such as changes in object positioning and/or the presence of strong extraneous gradients in the 2D projections (e.g., the presence of a metal biopsy needle). Furthermore, the self-calibration method could enable advanced 3D imaging methods that utilize non-circular orbits to expand the field of view, improve image quality (e.g., reduce cone-beam artifacts), and/or maximize local, task-dependent imaging performance, as in task-driven imaging. Future work includes extension of the algorithm to provide a basis for motion correction and evaluation in clinical image data.

This work shows the feasibility of using a "self" calibration directly from the acquired projection data in CBCT. The method is applicable to systems involving noncircular orbits and facilitates the realization of task-based imaging on sophisticated C-arm platforms.

The present invention carried out using a computer, non-transitory computer readable medium, or alternately a computing device or non-transitory computer readable medium incorporated into the scanner. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. Scanners generally have a console which is a proprietary master control center of the scanner designed specifically to carry out the operations of the scanner and receive the imaging data created by the scanner. Typically, this console is made up of a specialized computer, custom keyboard, and multiple monitors. There can be two different types of control consoles, one used by the scanner operator and the other used by the physician. The operator's console controls such variables as the thickness of the image, the amount of tube current/voltage, mechanical movement of the patient table and other radiographic technique factors. The physician's viewing console allows viewing of the images without interfering with the normal scanner operation. This console is capable of rudimentary image analysis. The operating console computer is a non-generic computer specifically designed by the scanner manufacturer for bilateral (input output) communication with the scanner. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

Additionally, future work will apply the self-calibrated geometry to iterative reconstruction methods such as penalized likelihood or other model-based image reconstruction methods, where accurate knowledge of scan-specific system geometry is expected to be just as important as it is for FBP reconstructions. Future work includes additional testing on the Zeego C-arm system, as well as modifying the registration algorithm for robust initialization. For example, in the case of a system with adjustable geometry, initialization of the first projection could be provided by basic input and each subsequent projection could be initialized using the estimated geometry of the previous projection in a bootstrapping manner. The system is also generally applicable as a refinement to systems that are believed to be well calibrated but may suffer slight irreproducibility. Similarly, the method allows reliable CBCT reconstruction in situations where the geometric calibration is no longer valid (e.g., out of date) and provides a potential sentinel to detect when geometric calibration has fallen out of tolerance.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for self-calibrating projection geometry for a volumetric image reconstruction comprising:
 selecting a prior volumetric representation of a patient;
 dividing a cone-beam computed tomography (CBCT) scan from a CBCT scanner to be self-calibrated into a number of projections;
 selecting a projection from the number of projections;
 registering the projection to the prior volumetric representation in order to determine a 9-degree-of freedom geometric calibration of the selected projection;
 applying the 9-degree-of-freedom geometric calibration of the selected projection;
 generating a projection matrix from the 9-degree-of-freedom geometric calibration of the selected projection; and
 generating and displaying a three-dimensional, volumetric reconstruction of the CBCT scan using a plurality of the projection matrix for self-calibration of the CBCT scanner.

2. The method of claim 1 further comprising using a preoperative CT as the prior volumetric representation of the patient.

3. The method of claim 1 further comprising using an CMA-ES optimization algorithm for applying a 9-degree-of-freedom geometric calibration of the selected projection.

4. The method of claim 1 further comprising using an NGI similarity metric for applying a 9-degree-of-freedom geometric calibration of the selected projection.

5. The method of claim 1 further comprising applying fixed intrinsic parameters such that the 9-degree-of-freedom geometric calibration is limited to a 6-degree-of-freedom geometric calibration.

6. The method of claim 1 further comprising initializing the 9-degree-of-freedom geometric calibration of the selected projection with the 9-degree-of-freedom geometric calibration result of another projection.

7. The method of claim 1 wherein the cone-beam computed tomography CBCT scan takes the form of a tomosynthesis scan and the volumetric reconstruction of the CBCT scan is instead a volumetric reconstruction of the tomosynthesis scan.

8. The method of claim 1 further comprising repeating the 9-degree-of-freedom, self-calibration for each of the projection of the number of projections.

9. The method of claim 1 further comprising performing an FDK three-dimensional, volumetric reconstruction.

10. The method of claim 1 further comprising performing an MBIR three-dimensional, volumetric reconstruction.

11. The method of claim 1 further comprising using a non-transitory computer readable medium programmed for executing steps of the method.

12. The method of claim 1 further comprising estimating intrinsic and extrinsic parameters of the selected projection using the 9-degree-of-freedom geometric calibration.

13. A system for self-calibrating projection geometry for a volumetric image reconstruction of a subject comprising:
 a cone-beam computed tomography (CBCT) scanner for generating CBCT image data for the subject, wherein the CBCT scanner is to be self-calibrated;
 a non-transitory computer readable medium programmed for:
 selecting a prior volumetric representation of a subject;
 dividing a CBCT scan into a number of projections;
 selecting a projection from the number of projections;
 registering the projection to the prior volumetric representation in order to determine a 9-degree-of freedom geometric calibration of the selected projection;
 applying a 9-degree-of-freedom geometric calibration of the selected projection;
 generating a projection matrix from the 9-degree-of-freedom geometric calibration of the selected projection;
 generating and displaying a three-dimensional, volumetric reconstruction of the CBCT scan using a plurality of the projection matrix for self-calibration of the CBCT scanner.

14. The system of claim 13 further comprising using a preoperative CT as the prior volumetric representation of the patient.

15. The system of claim 13 further comprising using a CMA-ES optimization algorithm for applying a 9-degree-of-freedom geometric calibration of the selected projection.

16. The system of claim 13 further comprising using a NGI similarity metric for applying a 9-degree-of-freedom geometric calibration of the selected projection.

17. The system of claim 13 further comprising applying fixed intrinsic parameters such that the 9-degree-of-freedom geometric calibration is limited to a 6-degree-of-freedom geometric calibration.

18. The system of claim 13 further comprising initializing the 9-degree-of-freedom geometric calibration of the selected projection with the 9-degree-of-freedom geometric calibration result of another projection.

19. The system of claim 13 wherein the cone-beam computed tomography CBCT scan takes the form of a tomosynthesis scan and the volumetric reconstruction of the CBCT scan is instead a volumetric reconstruction of the tomosynthesis scan.

20. The system of claim 13 further comprising repeating the 9-degree-of-freedom, self-calibration for each of the projection of the number of projections.

* * * * *